(12) United States Patent
Chang et al.

(10) Patent No.: US 7,785,872 B2
(45) Date of Patent: Aug. 31, 2010

(54) NUCLEIC ACIDS FOR ENHANCING GENE EXPRESSION AND USE THEREOF

(75) Inventors: Margaret Dah-Tsyr Chang, Hsinchu (TW); Chia-Chin Sheu, Kuei Shan Hsiang (TW)

(73) Assignee: Simpson Biotech Co., Ltd., Taoyuan (TW)

( * ) Notice: Subject to any disclaimer, the term of this patent is extended or adjusted under 35 U.S.C. 154(b) by 0 days.

(21) Appl. No.: 11/006,817

(22) Filed: Dec. 8, 2004

(65) Prior Publication Data

US 2007/0122876 A1 May 31, 2007

(51) Int. Cl.
*C12N 15/00* (2006.01)
*C12N 15/62* (2006.01)
*C12N 15/67* (2006.01)
*C12N 15/12* (2006.01)
*C12P 21/06* (2006.01)

(52) U.S. Cl. .................. 435/320.1; 530/23.1; 530/23.4; 530/24.1; 435/69.1; 435/91.4

(58) Field of Classification Search ....................... None
See application file for complete search history.

(56) References Cited

U.S. PATENT DOCUMENTS

| | | | |
|---|---|---|---|
| 6,214,547 B1 * | 4/2001 | Kjeldsen et al. ................ | 435/6 |
| 2003/0022280 A1 * | 1/2003 | Takagi et al. ............... | 435/69.1 |
| 2005/0036987 A1 * | 2/2005 | Pawelek et al. ............ | 424/93.2 |

FOREIGN PATENT DOCUMENTS

WO    WO 03070957 A2 *  8/2003

OTHER PUBLICATIONS

Liu SH, Chou WI, Sheu CC, Chang MD. Improved secretory production of glucoamylase in *Pichia pastoris* by combination of genetic manipulations. Biochem Biophys Res Commun. Jan. 28, 2005;326(4):817-24.*
Cregg, James M., et al., "Recombinant Protein Expression in *Pichia pastoris*", Molecular Biotechnology, (2000), 16:23-51.
Outchkourov, Nikolay S., et al., "Optimization of the Expression of Equistatin in *Pichia pastoris*", Protein Expression and Purification, (2002), 24:18-24.
Vassileva, Ana, et al., "Expression of hepatitis B surface antigen in the methylotrophic yeast *Pichia pastoris* using the GAP promoter", Journal of Biotechnology, (2001), 88:21-35.
Vassileva, Ana, et al., Effect of Copy Number on the Expression Levels of Hepatitis B Surface Antigen in the Methylotrophic Yeast *Pichia pastoris*, Protein Expression and Purification, (2001), 21:71-80.
Sears, Irina B., et al., "A Versatile Set of Vectors for Constitutive and Regulated Gene Expression in *Pichia pastoris*", Yeast, (1998), 14:783-790.
Cavener, Douglas, R., "Eukaryotic start and stop translation sites", Nucleic Acids Research, (1991), 19:12:3185-3192.
Briand, Laïc, et al., Optimization of the Production of a Honeybee Odorant-Binding Protein by *Pichia pastoris*, Protein Expression and Purification, (1999), 15:362-369.
Raemaekers, Romaan J.M., et al., "Functional phytohemagglutinin (PHA) and *Galanthus nivalis* agglutinin (GNA) expressed in *Pichia pastoris*", Eur. J. Biochem. (1999), 265:394-403.
Koganesawa, Nozomi, et al., "Construction of an expression system of insect lysozyme lacking thermal stability: the effect of selection of signal sequence on level of expression in the *Pichia pastoris* expression system", Protein Engineering, (2001), 14:9:705-710.
Kowalski, Jean M.,et al., "Protein Folding Stability Can Determine the Efficiency of Escape from Endoplasmic Reticulum Quality Control", The Journal of Biological Chemistry, (1998), 273:31: 7/31 Issue: 19453-19458.
Rossini, Dominique, et al., "In *Saccharomyces cerevisiae*, Protein Secretion into the Growth Medium Depends on Environmental Factors", Yeast, (1993), 9:77-84.
Coutinho, Pedro M., et al., "Glucoamylase Structural, Functional, and Evolutionary Relationships", Proteins: Structures, Function, and Genetics, (1997) 29:334-347.
Toikkanen, Jaana, H., et al., "The β Subunit of the Sec61p Endoplasmic Reticulum Translocon Interacts with the Exocyst Complex in *Saccharomyces cerevisiae*", The Journal of Biological Chemistry, (2003), 278:23: 6/6 Issue:20946-20953.
Sakai, Yasuyoshi et al., High-level secretion of fungal glucoamylase using the *Candida boidinii* gene expression system, Biochimica et Biophysica Acta, (1996), 81-87.
Sreekrishna, Koti, et al., "Strategies for optimal synthesis and secretion of heterologous proteins in the methylotrophic yeast *Pichia pastoris*", Gene, (1997), 55-62.
Salminen, Antti, et al., "A *ras*-like Protein Is required for a Post-Golgi Event in Yeast Secretion", Cell, (1987), 49:527-538.
Jiang, Yu, et al., "Bet2p and Mad2p are components of a prenyltransferase that adds geranylgeranyl onto Ypt1p and Sec4p", Nature, (1993), 366:84-86.
Lipschutz, Joshua, et al., "Exocytosis: The Many Masters of the Dispatch Exocyst", Current Biology, (2002), 12:R212-214.
Huynh, Trang Thi Ngoc, et al., "The Genes of Two G-Proteins Involved in Protein Transport in *Pichia pastoris*", Biochemical and Biophysical Research Communications, (2001), 280:454-459.
Oka, Chitoshi, et al., "Human Lysozyme Secretion Increased by Alpha-factor Pro-sequence in *Pichia pastoris*", Biosci. Biotechnol. Biochem., (1999), 63:11:1977-1983.
Kjeldsen, Thomas, et al., "α-Factor pro-peptide N-linked oligosaccharides facilitate secretion of the insulin precursor in *Saccaromyces cerevisiae*", Biotechnol. Appl. Biochem., (1998), 27:109-115.
Lazar, Thomas, et al., "Vesicular transport: how many Ypt/Rab-GTPases make a eukaryotic cell", TIBS 22, (1997), 468-472.
Liu, Shi-Hwei, "Improved Secretory Production of Glucoamylase in *Pichia pastoria* by Combination of Genetic Manipulations." Biochemical and Biophysical Research Communication 326 (2005) 817-824. Eisevier Inc.

* cited by examiner

*Primary Examiner*—Maria Marvich
(74) *Attorney, Agent, or Firm*—WPAT, P.C.; Anthony King

(57) ABSTRACT

The present invention relates to a method for producing a protein, novel nucleic acid fragment, an expression vector, and a method for enhancing the protein production in *Pichia*.

The present invention provides that the combination of the modified signal peptide, increased copy number of the gene, and/or overexpressed Sec4p resulted in high level secretion of proteins.

2 Claims, 5 Drawing Sheets

A

B

NUCLEIC ACIDS FOR ENHANCING GENE EXPRESSION AND USE THEREOF

FIELD OF INVENTION

The invention relates generally to a method for producing a protein, a novel nucleic acid fragment, an expression vector, and a method for enhancing the protein production in *Pichia*.

BACKGROUND OF INVENTION

The methylotrophic yeast *Pichia pastoris* has been developed as a widely used host organism for recombinant protein production. The majority of the referred examples concern heterologous proteins that have been secreted to the growth medium of *Pichia pastoris*. In some cases exceptionally high yields have been obtained, such as human serum albumin and murine gelatins, whereas the secretion levels of many other proteins were significantly lower. e.g., J. M. Cregg., et al., Recombinant protein expression in *Pichia pastoris*, Mol. Biotechnol. 16 (2000) 23-52.

Potential Bottlenecks for Protein Secretion Include:

1. Codon usage of the expressed gene, e.g., N. S. Outchkourov., et al., Optimization of the expression of equistatin in *Pichia pastoris*, Protein Expr. Purif. 24 (2002) 18-24;
2. Copy number of the gene, e.g., A. Vassileva., et al., Expression of hepatitis B surface antigen in the methylotrophic yeast *Pichia pastoris* using the GAP promoter, J. Biotechnol. 88 (2001) 21-35; A. Vassileva., et al., Effect of copy number on the expression levels of hepatitis B surface antigen in the methylotrophic yeast *Pichia pastoris*, Protein Expr. Purif. 21 (2001) 71-80;
3. The efficiency and strength of promoters, e.g., I. B. Sears., et al., A versatile set of vectors for constitutive and regulated gene expression in *Pichia pastoris*, Yeast 14 (1998) 783-90;
4. Translation signals, e.g., D. R. Cavener., et al., Eukaryotic start and stop translation sites, Nucleic Acids Res. 19 (1991) 3185-92;
5. Signal peptides, e.g., L. Briand., et al., Optimization of the production of a honeybee odorant-binding protein by *Pichia pastoris*, Protein Expr. Purif. 15 (1999) 362-9; Z. I. Crawford K., et al., *Pichia* secretory leader for protein expression, U.S. Pat. No. 6,107,057 (2000); R. J. Raemaekers., et al., Functional phytohemagglutinin (PHA) and Galanthus nivalis agglutinin (GNA) expressed in *Pichia pastoris* correct N-terminal processing and secretion of heterologous proteins expressed using the PHA-E signal peptide, Eur. J. Biochem. 265 (1999) 394-403; N. Koganesawa., et al., Construction of an expression system of insect lysozyme lacking thermal stability: the effect of selection of signal sequence on level of expression in the *Pichia pastoris* expression system, Protein Eng. 14 (2001) 705-10;
6. Processing and folding in the endoplasmic reticulum (ER) and Golgi, e.g., J. M. Kowalski., et al., Protein folding stability can determine the efficiency of escape from endoplasmic reticulum quality control, J. Biol. Chem. 273 (1998) 19453-8;
7. Extracellular secretion: e.g., D. Rossini., et al., Alberghina, In *Saccharomyces cerevisiae*, protein secretion into the growth medium depends on environmental factors, Yeast 9 (1993) 77-84; and
8. Protein turnover by proteolysis. e.g., J. M. Cregg., et al., Recombinant protein expression in *Pichia pastoris*, Mol. Biotechnol. 16 (2000) 23-52.

To overcome the problems encountered in protein expression, proper consideration of the influencing factors should be taken. A practical solution is to identify the major bottleneck of the production system, which in general is both host strain- and product-dependent.

Since the bottlenecks in producing different heterologous proteins remains to be case specific, a need in the art for techniques that will facilitate high-yield protein production in yeasts, including *Pichia pastoris*, of economic importance.

Term Definition

The following definitions are offered for purposes of illustration, not limitation, in order to assist with understanding the discussion that follows.

In accordance with the present invention there may be employed conventional molecular biology, microbiology, and recombinant DNA techniques within persons skilled in the art. Such techniques are explained fully in the literature.

A "polynucleotide" is a single- or double-stranded polymer of deoxyribonucleotide or ribonucleotide bases, the sequence of the polynucleotide is the actual sequence of the bases read from the 5' to the 3' end of the polymer. Polynucleotides include RNA and DNA, and may be isolated from natural sources, synthesized in vitro, or prepared from a combination of natural and synthetic molecules.

A "nucleic acid" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA" is a DNA molecule that has undergone a molecular biological manipulation.

A DNA "coding sequence" or an is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

An expression vector is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Transcriptional and translational control sequences are DNA regulatory sequences, such as promoters, enhancers, terminators, and the like, that provide for the expression of a coding sequence in a host cell e.g. in eukaryotic cells, polyadenylation signals are control sequences.

A "signal sequence" is a DNA sequence that encodes a polypeptide (a "signal peptide" that, as a component of a larger polypeptide, directs the larger polypeptide through a secreted pathway of a cell in which it is synthesized. The larger polypeptide is commonly cleaved to remove the signal peptide during transit through the secreted pathway.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A chromosomal gene is rendered "non-functional" if the polypeptide that the gene encodes can no longer be expressed in a functional form. Such non-functionality of a gene can be induced by a wide variety of genetic manipulations or alterations as known in the art.

"Operably linked", when referring to DNA segments, indicates that the segments are arranged so that they function in concert e.g. the transcription process takes place via the RNA-polymerase binding to the promoter segment and proceeding with the transcription through the coding segment until the polymerase stops when it encounters a transcription terminator segment.

As used herein the term "nucleic acid fragment" is intended to indicate any nucleic acid molecule of cDNA, genomic DNA, synthetic DNA or RNA origin. The term "fragment" is intended to indicate a nucleic acid segment which may be single- or double-stranded, and which may be based on a complete or partial naturally occurring nucleotide sequence encoding a polypeptide of interest. The fragment may optionally contain other nucleic acid segments.

The nucleic acid fragment of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques.

Furthermore, the nucleic acid fragment may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid fragment, in accordance with standard techniques. The nucleic acid fragment may also be prepared by polymerase chain reaction using specific primers, for instance as described in U.S. Pat. No. 4,683,202.

The term nucleic acid fragment may be synonymous with the term "expression cassette" when the nucleic acid fragment contains the control sequences necessary for expression of a coding sequence of the present invention.

The term "control sequences" is defined herein to include all components that are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence that is recognized by a host cell for expression of the nucleic acid sequence.

The promoter sequence contains transcription and translation control sequences that mediate the expression of the polypeptide. The promoter may be any nucleic acid sequence that shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide-coding region, which codes for an amino acid sequence linked to the amino terminus of the polypeptide which can direct the expressed polypeptide into the cell's secreted pathway of the host cell. The 5' end of the coding sequence of the nucleic acid sequence may inherently contain a signal peptide-coding region naturally linked in translation reading frame with the segment of the coding region which encodes the secreted polypeptide. Alternatively, the 5' end of the coding sequence may contain a signal peptide-coding region which is foreign to that portion of the coding sequence which encodes the secreted polypeptide.

A foreign signal peptide-coding region may be required where the coding sequence does not normally contain a signal peptide-coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide-coding region may be obtained from a glucoamylase or an amylase gene from an Aspergillus species, a lipase or proteinase gene from a *Rhizomucor* species, the gene for the alpha-factor from *Saccharomyces cerevisiae*, an amylase or a protease gene from a *Bacillus* species, or the calf preprochymosin gene. However, any signal peptide coding region capable of directing the expressed polypeptide into the secreted pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Examples of suitable promoters for directing the transcription of the nucleic acid fragments of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus subtilis* alkaline protease gene, the *Bacillus licheniformis* alpha-amylase gene (amyL), the *Bacillus stearothennophilus* maltogenic amylase gene (amyM), the *Bacillus amyloliquefaciens* alpha-amylase gene (amyQ), the *Bacillus amyloliquefaciens* ban amylase gene, the *Bacillus licheniformis* penicillinase gene (penP), the *Bacillus subtilis* xylA and xylB genes, and the prokaryotic beta-lactamase gene, as well as the tac promoter.

The present invention also relates to expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid fragment comprising the sequence into an appropriate vector for expression. In creating the expression vector, the coding sequence is located in the vector so that the coding sequence is operably linked with the appropriate control sequences for expression, and possibly secretion.

The expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more "selectable markers" which permit easy selection of transformed cells. A selectable marker is a gene the product of which provides for biocide, antibiotic or viral resistance, resistance to heavy metals, prototrophy to auxotrophs, and the like.

Antibiotic selectable markers confer antibiotic resistance to such antibiotics as ampicillin, kanamycin, chloramphenicol, erythromycin, tetracycline, zeocine, neomycin, hygromycin or methotrexate.

The vectors, or smaller parts of the vectors, may be integrated into the host cell genome when introduced into a host cell. For chromosomal integration, the vector may rely on the nucleic acid sequence encoding the polypeptide or any other element of the vector for stable integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

The copy number of a vector, an expression cassette, an amplification unit, a gene or indeed any defined nucleotide sequence is the number of identical copies that are present in a host cell at any time. A gene or another defined chromosomal nucleotide sequence may be present in one, two, or more copies on the chromosome. An autonomously replicating vector may be present in one, or several hundred copies per host cell.

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., an eukaryote.

The transformation of a host cell may, for instance, be effected by using competent cells, by electroporation, or by chemical such as lithium chloride method.

The transformed host cells described above are cultured in a suitable nutrient medium under conditions permitting the expression of the desired polypeptide, after which the resulting polypeptide is recovered from the cells, or the culture broth.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art.

If the polypeptide is secreted into the nutrient medium, the polypeptide can be recovered directly from the medium. If the polypeptide is not secreted, it is recovered from cell lysates. The polypeptide are recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isdelectric focusing (IEF), differential solubility (e.g., ammonium sulfate precipitation), or extraction.

"GA" represents herein *Rhizopus oryzae* glucoamylase, one of the most important enzymes in the fermentation industry for its practical usage on saccharifying starch in alcohol production; see e.g., P. M. Coutinho. et al., Glucoamylase structural, functional, and evolutionary relationships, Proteins 29 (1997) 334-47.

"MSP" represents herein a modified signal peptide; a signal peptide is usually at the N terminus and normally absent from the mature protein. Normally refers to the sequence (about 20 amino acids) that interacts with signal recognition particle and directs the ribosome to the endoplasmic reticulum where co-translational insertion takes place. Signal peptides are highly hydrophobic but with some positively charged residues. The signal sequence is normally removed from the growing peptide chain by signal peptidase, a specific protease located on the cisternal face of the endoplasmic reticulum see e.g., Z. I. Crawford K., et al., *Pichia* secreted leader for protein expression, U.S. Pat. No. 6,107,057.

"Copy number" represents herein the number of copies of a given gene present in a cell or nucleus. An increase in gene dosage can result in the formation of higher levels of gene product, provided that the gene is not subject to autogenous regulation, see e.g., A. Vassileva., et al., Effect of copy number on the expression levels of hepatitis B surface antigen in the methylotrophic yeast *Pichia pastoris*, Protein Expr. Purif. 21 (2001) 71-80

"SEC4" represents herein a GTP-binding protein of the rab branch of the ras superfamily that functions as a nucleotide dependent switch on the surface of secreted vesicles. On the secreted vesicles Sec4 promotes the protein-protein interactions among the exocyst components, and the assembly of the exocyst complex eventually links the secreted vesicles to specific domains of the plasma membrane marked by another exocyst protein Sec3. see e.g., J. H. Toikkanen., et al., The beta subunit of the Sec61p endoplasmic reticulum translocon interacts with the exocyst complex in *Saccharomyces cerevisiae*, J. Biol. Chem. 278 (2003) 20946-53.

SUMMARY OF INVENTION

Figure 1:
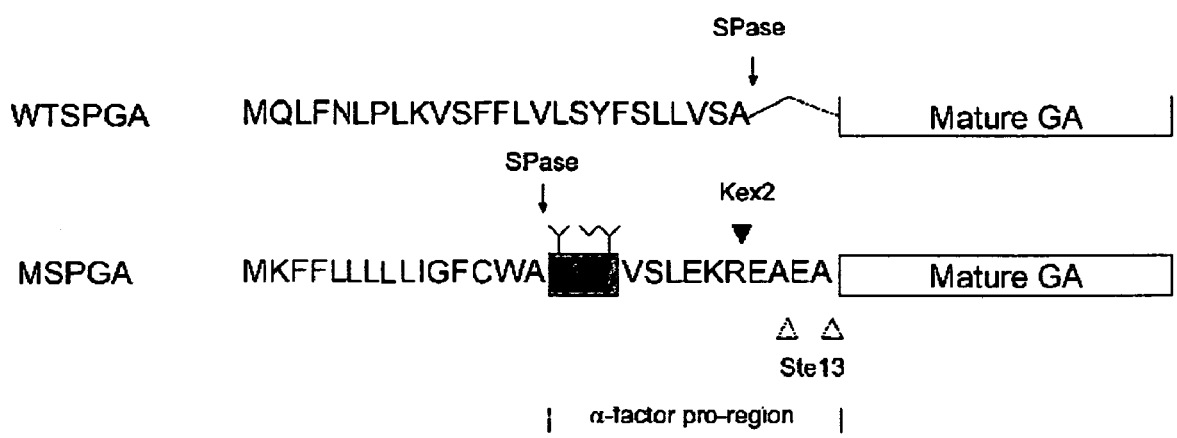
FIG. 1 is the diagram of WTSPGA and MSPGA genes. The 25-aa sequence of WTSPGA (SEQ ID NO:14) and the first 15-aa of MSP (SEQ ID NO: 15) are shown. An S8L substitution in MSP is underlined (SEQ ID NO:16). The subsequent 70 amino acids residues of MSP indicate the pro-region of the signal peptide of *Saccharomyces cerevisiae* α-mating factor. Gray box contains 60 amino acids part of pro-region of signal peptide of *Saccharomyces cerevisiae* α-mating factor, where the potential N-glycosylation sites are shown by forked symbols. The arrows indicate the location of the punitive cleavage site of signal peptidase (SPase). C-terminal 10 aa sequence of MSP (SEQ ID NO:16. The closed arrowhead indicates the Kex2 cleavage site, and the open arrowheads indicate the STE13 cleavage site.

The present invention provides a method for producing a protein in a host cell comprising the steps of:
(a) constructing an expression vector having a formula:

$$(AA'xB)n$$

wherein
A represents a sequence encoding a promoter operably linked to a signal peptide;
A' represents a sequence encoding a pro-region of yeast α-mating factor;
B represents a sequence encoding a protein;
x represents 0-1;
n represents 1-20;
provided that if x is 0 then n is not 1;
(b) transforming said vector to a host cell; and
(c) expressing said peptide in said host cell.

In a preferred embodiment, the present invention provides methods to further positively regulate the protein production in host cells by transforming the host with one more expression vector of the present invention.

In one aspect, the present invention provides to a nucleic acid fragment having a formula:

$$(AA'xB)n$$

wherein
A represents a sequence encoding a promoter operably linked to a signal peptide;
A' represents a sequence encoding a pro-region of yeast α-mating factor;
B represents a sequence encoding a protein;
x represents 0-1;
n represents 1-20; and
provided that if x is 0 then n is not 1.

In another aspect, the present invention provides an expression vector for enhancing protein production comprising a sequence encoding Rab GTPase.

In further aspect, the present invention also provides a method for enhancing protein production in *Pichia* comprising the steps of
(a) transforming *Pichia* with the expression vector of the invention; and;
(b) expressing the protein in *Pichia*.

DETAILED DESCRIPTION OF THE INVENTION

To date, numerous efforts have been made to fulfill the purpose of realizing quantity production of a useful protein by the use of recombination DNA techniques.

The technique of recombination DNA for the quantity production of a useful protein basically comprises a host, a vector, and a gene coding a useful protein.

The hosts which are usable for this technique include prokaryotes such as *Escherichia coli* and *Bacillus subtilis* and eukaryotes such as yeast, animal cells, and plant cells. In the selection of a host for a particular recombination, due consideration is paid to the characterization of a protein subjected to expression and the use for which the produced protein is intended.

As regards the vector to be used for the recombination, a large number of widely varying vectors have been developed to date. There are four basic functions which are required of a vector; (1) an ability to form an in vitro recombinant with a DNA which codes the protein aimed at, (2) an ability to attain growth in the cell of the host aimed at, (3) an ability to attain introduction in the cell of the host aimed at, and (4) ability to effect specific detection of a cell possessing a recombinant DNA. For the purpose of fulfilling quantity production of the useful protein, the vector is further required to possess these additional functions; (5) ability to possess a strong promoter and a terminator (DNA sequences concerning expression) and (6) an ability to possess a signal sequence (DNA sequences concerning secretion).

A strong promoter is necessary for and indispensable to quantity production of a protein. The secretion of a mass-produced protein by a signal sequence is effective in preventing intracellular accumulation of a protein harmful to the host, precluding decomposition of a product by a protease in the cell, and simplifying and economizing the process of purification of a useful protein which has heretofore entailed expenditure of great labor and cost.

Owing to the advantages mentioned above, efforts are being continued in research and development of strong promoters and signal sequences excelling in efficiency of secretion.

In the case of *Escherichia coli* as a prokaryote, a lac promoter for lactose operon, a trp promoter for tryptophan operon, an lpp promoter and a signal sequence for an outer-membrane protein gene, and a lacUV5 promoter and a tac promoter as improved versions thereof have been developed. In the case of *Bacillus subtilis*, a penP for an enzyme penicillinase gene outside bacteria and a promoter and a signal sequence for α-amylase have been developed.

In the case of yeasts as a eukaryote, promoters for a group of glycolytic enzymes have been demonstrated as effective for strong and over expression of proteins. For example, promoters and α-factors and signal sequence of such α-factor for genes such as 3-phosphoglycerate kinase (PGK), glyceraldehyde triphosphoric acid dehydrogenase (GLD), enolase (ENO), triose phosphoric acid isomerase (TPI), alcohol dehydrogenase (ADH), acidic phosphatase (PHO), and the galactose metabolic system (GAL), have been developed and put to use.

The number of cases of successful development of promoters usable for cells of higher animals is still small. Though promoters for early gene and late gene of the virus SV40 attaining satisfactory propagation in the cell of monkey, a promoter for an ICP gene of HSV, a promoter for an early gene of vaccinia virus, a promoter for a chicken actin, a promoter for a human EF-1α gene, and an IgG H chain promoter have been developed, they are not fit for the purpose of quantity production of useful proteins.

As regards promoters which are usable for the technique of gene recombination using a plant as a host, a promoter for the 35S gene of a cauliflower mosaic virus, a promoter for a nopalin synthetic gene of a Ti plasmid, and an ORF12 promoter for an Ri plasmid have been developed. Again, these promoters are unfit for the purpose of over-production of useful proteins.

Recently, development of systems for secreted production of useful proteins by the use of a mold particularly of genus Aspergillus has come to appear in literature. The secreted production of such proteins as lipase and prochymosin by the use of a promoter for a glucoamylase gene of *Aspergillus niger* and a signal sequence has been realized.

This statement does not necessarily mean that the use of systems capable of expression and secretion of mold of genus *Aspergillus* permits efficient and secreted over production of all useful proteins. Thus, efforts are being continued in research and development of a system capable of more efficient expression and secretion.

Incidentally, a technique of gene recombination using a basidiomycete as a host remains yet to be established. The basidiomycetes include numerous useful fungi such as edible mushroom, fungi producing physiologically active substances, fungi capable of decomposing lignin and useful for biological pulping and biobleaching, and fungi decomposing cellulose and saccharifying lignous components. Attempts at improving and fortifying the characteristics of these fungi and breeding these fungi have been made heretofore with a method resorting to mating, a method resorting to acquisition of a variant, and a method resorting to cell fusion, for example. If a method for molecular breeding by the use of the technique of gene recombination is realized, it would allow easy acquisition of excellent strains.

No promoter has been so far developed which is used effectively for basidiomycetes. Virtually no successful cloning of a gene for providing a promoter has yet been reported in literature, except for a report concerning a ligninase gene obtained by cloning with a microorganism of genus *Phanerochaete chrysosporium*. This gene is characterized by expressing ligninase by virtue of secondary metabolism and the extent of this expression is not appreciably large. Thus, the gene does not deserve to be called an effective promoter. In the circumstances, a desire has been expressed in the industry to develop a promoter and a signal sequence which are capable of effecting efficient secretion and expression of useful proteins with basidiomycete. The promoter and signal sequence thus yearned for are required to effect strong expression in a wide variety of hosts and possess a signal sequence for allowing secretion of a protein produced by the expression.

The present inventors have pursued a diligent study with a view to fulfilling the demand for development of a promoter, a signal sequence, and a terminator capable of secreted production of all useful proteins in large amounts. They have consequently succeeded in developing novel DNA's, i.e. a promoter, a signal sequence, and a terminator, concerning the expression and secretion, which attain secreted production of glucoamylase in a *Pichia pastoris* in a large amount. The present invention combines modified signal peptide (MSP), increased copy number of the gene, and overexpressed Sec4p to achieve the improvement in heterologous protein production.

The present invention provides a method for producing a protein in a host cell comprising the steps of:
A represents a sequence encoding a promoter operably linked to a signal peptide;
A' represents a sequence encoding a pro-region of yeast α-mating factor;
B represents a sequence encoding a protein;
x represents 0-1;
n represents 1-20;
provided that if x is 0 then n is not 1;
(b) transforming the vector to the host cell; and
(c) expressing the protein in the host cell.

In formula I of the present invention, parameter "A" represents a sequence encoding a promoter operably linked to a signal peptide. The preferred embodiment of the signal peptide is one which could be recognized by fungus. The more preferred embodiment of the signal peptide is a mammalian (such as mouse) signal peptide of salivary α-amylase. The further more preferred embodiment of the signal peptide is a signal peptide of mouse salivary α-amylase in which the Serine at position 8 amino acid is replaced by Leucine, Isoleucine, Valine, Alanine, Glycine or Phenylalanine. The most preferred embodiment of the signal peptide is a signal peptide of mouse salivary α-amylase in which the Serine at position 8 amino acid is replaced by Leucine (S8L).

In formula I of the present invention, parameter "A'" represents a sequence encoding a pro-region of yeast α-mating factor. The most preferred embodiment of "A'" is pro-region sequence of *Saccharomyces cerevisiae* α-mating factor (SEQ ID NO: 1).

In formula I of the present invention, parameter "B" represents sequence encoding a protein. In particular, the preferred embodiment is a secertory protein selected from those stated in the document entitled "Heterologous Proteins Expressed in *Pichia pastoris*." The more preferred embodiment is the protein denoted by S (Secreted) in comment column (mode, amount, signal sequence) of the same document. The further more preferred embodiment is protein denoted by S (Secreted) and α-MF in comment column (mode, amount, signal sequence) of the above mentioned document.

The further more preferred embodiment of the protein produced by the method of the invention is a fungus secertory protein such as *Alternaria alternata* Alt a 1 allergen, *Alternaria alternata* rAlt a 2 allergen, *Aspergillus awamori* glucoamylase, *Aspergillus awamori* glucoamylase catalytic domain, *Aspergillus fumigatus* Asp f 2 allergen, *Aspergillus fumigatus* catalase L, *Aspergillus fumigatus* dipeptidyl peptidase IV (DPP IV), *Aspergillus fumigatus* dipeptidyl peptidase V (DPP V), *Aspergillus fumigatus* phytase, *Aspergillus giganteus* alpha-sarcin ribotoxin, *Aspergillus niger* β-glucosidase, *Aspergillus niger* phytase (phyA), *Candida guilliernondii* xylose reductase gene (xylI), *Aspergillus niger* endo-β-1,4-xylanase, *Candida rugosa* lipase 1 (CRL), *Fusarium solani* pectate lyase (pelC), *Fusarium solani* pectate lyase (pelD), *Geotrichum candidum* lipase isoenzymes, *Phytophthora cryptogea* β-cyptogein, *Rhizopus oryzae* lipase, *Saccharomyces cerevisiae* invertase, *Saccharomyces cerevisiae* Ktr1p, *Saccharomyces cerevisiae* (α-1,2-mannosyltransferase), *Schizophyllum commune* vitamin B2-aldehyde-forming enzyme, *Trametes versicolor* (white rot fungus) laccase (lccI), *Trichoderma harzianum* β-(1-6)-glucanase, *Candida albicans* MNT1 mannosyltransferase, *Candida antarctica* Lipase B, *Candida rugosa* LIP2 lipase, *Candida rugosa* lip4 lipase, *Kurtzmanomyces* sp. 1-11 lipase, *Metarhizium anisopliae* chymotrypsin, *Mucor pusillus* rennin, *Neurospora crassa* NOP-1, *Neocallimastix patriciarum* cellulase 6A-*Candida Antarctica* lipase B fusion protein, *Phanerochaete chrysosporium* glyoxal oxidase, *Phanerochaete chrysosporium* cellobiose dehydrogenase, *Phanerochaete chrysosporium* β-glucosidase, *Phaeseolus vulgaris* aspartic protease, Barley glucosidase, *Pleurotus sajor-caju* laccase isozyme, *Pycnoporus cinnabarinus* I-937 laccase, *Saccharomyces cerevisiae* Hsp70, *Saccharomyces cerevisiae* Kex 2p, *Trichodenna reesei* cellobiohydrolase I, *Trichoderma reesei* cellobiohydrolase Cel7A or *Trichoderma reesei* 1,2-α-kD-mannosidase.

The more particularly preferred embodiment of the protein is a secertory enzyme of fungus such as glucoamylase (GA)

of *Rhizopus oryzae*, glucoamylase of *Aspergillus niger*, glucoamylase of *Aspergillus awamori*, glucoamylase catalytic domain of *Aspergillus awamori*, lipase of *Rhizopus oryzae*. In the most preferred embodiment of the protein is glucoamylase of *Rhizopus oryzae*.

In one embodiment of present invention, the parameter "n" in formula I represents 1-20. In the preferred embodiment, n is 2-10. In the more preferred embodiment, n is 3-7. In the most preferred embodiment, n is 7.

Expression of R. *oryzae* Glucoamylase (GA) in *Pichia*

*Rhizopus oryzae* glucoamylase (GA) is one of the most important enzymes in the fermentation industry for its practical usage on saccharifying starch in alcohol production. e.g., P. M. Coutinho., et al., Glucoamylase structural, functional, and evolutionary relationships, Proteins 29 (1997) 334-47. We have previously observed that the secretion level of *R. oryzae* GA in *Pichia pastoris* possessing the original signal peptide of GA and a single copy of expression cassette was much lower than that of *Candida boidinii*. e.g., Y. Sakai, M. et al., High-level secretion of fungal glucoamylase using the *Candida boidinii* gene expression system, Biochim. Biophys. Acta. 1308 (1996) 81-7. Although *Pichia pastoris* and *C. boidinii* are both methylotrophic yeast, the secretion of *R. oryzae* GA seems to encounter more bottlenecks in *Pichia pastoris*. Various strategies for secretion of heterologous proteins have given some new insights into the intricacies of the *Pichia pastoris* expression system. e.g., K. Sreekrishna, R, et al., Strategies for optimal synthesis and secretion of heterologous proteins in the methylotrophic yeast *Pichia pastoris*, Gene 190 (1997) 55-62. Accordingly, in a preferred embodiment of the present invention, the GA protein secretion level in *Pichia pastoris* by means as such that the modified signal peptide and increased copy number of GA was engineered.

Modified Signal Peptide (MSP) and Gene Copy Number in Protein Production Enhancement To enhance the secretion level of GA in *Pichia pastoris*, a modified signal peptide (MSP) was designed to replace the original signal peptide of GA and recombinant clones with increased copy number of GA was screened.

In one aspect, the present invention provides a method which is capable of further positively regulating the protein yield by transforming the host cells with a vector which comprising the sequence encoding Rab GTPase. In the preferred embodiment, the vector comprising the sequence encoding a Rab GTPase selected from the group consisting of Sec3, Sec4, Sec5, Sec9, Sec15 and homologous thereof. In the most preferred embodiment, the vector comprising the sequence encoding Sec4 (SEQ ID NO: 13), which is cloned from genomic DNA of *Pichia pastoris*.

SEC4

Sec4p belongs to the Rab family of GTP binding proteins which are important regulators of all vesicular traffic events. It is essential for targeting the secreted vesicles to the plasma membrane as well as the post-Golgi event in yeast secretion. e.g., A. Salminen., et al., A ras-like protein is required for a post-Golgi event in yeast secretion, Cell 49 (1987) 527-38. During protein secretion process, Sec4p is anchored to vesicle membrane through a geranyl-geranylated C-terminus and further transported to the plasma membrane after vesicle docking. e.g., Y. Jiang., et al., Bet2p and Mad2p are components of a prenyltransferase that adds geranylgeranyl onto Ypt1p and Sec4p, Nature 366 (1993) 84-6. Genetic analysis suggested that Sec4p acts upstream of the exocyst, an effector for Sec4p, and targets secreted vesicles to sites of exocytosis in yeast. See e.g., J. H. Lipschutz., et al., Exocytosis: the many masters of the exocyst, Curr. Biol. 12 (2002) R212-4.

Although the function of Sec4p in *Pichia pastoris* is rarely discussed in terms of its role in protein secretion, the amino acid sequence of *Pichia pastoris* Sec4p matches nicely to other yeast Sec4p sequences with conservation of regions spanning domains involved in nucleotide binding and hydrolysis. e.g., T. T. Huynh., et al., The genes of two G-proteins involved in protein transport in *Pichia pastoris*, Biochem. Biophys. Res. Commun. 280 (2001) 454-9. Here we also investigated the functional role of Sec4p in production of R. *oryzae* GA in *Pichia pastoris*.

Preferably, the host used in present invention is a yeast, further more preferably, a yeast selected from the group consisting of Silk worm *Bombyx mori*, *Hansenula polymorpha*; *Saccharomyces cerevisiae*; *Pichia pastoris*, and *Kluyveromyces lactis*, and the most preferably, *Pichia pastoris*.

The present invention also provides a nucleic acid fragment having a formula I:

$$(AA'xB)n$$

wherein

A represents a sequence encoding a promoter operably linked to a signal peptide;

A' represents a sequence encoding a pro-region of yeast α-mating factor;

B represents a sequence encoding a protein;

x represents 0-1;

n represents 1-20; and provided that if x is 0 then n is not 1.

In formula I of the present invention, parameter "A" represents a sequence encoding a promoter operably linked to a signal peptide. The preferred embodiment of the signal peptide is one which could be recognized by fungus. The more preferred embodiment of the signal peptide is a mammalian (such as mouse) signal peptide of salivary α-amylase. The further more preferred embodiment of the signal peptide is a signal peptide of mouse salivary α-amylase in which the Serine at position 8 amino acid is replaced by Leucine, Isoleucine, Valine, Alanine, Glycine or Phenylalanine. The most preferred embodiment of the signal peptide is a signal peptide of mouse salivary α-amylase in which the Serine at position 8 amino acid is replaced by Leucine (S8L).

In formula I of the present invention, parameter "A'" represents a sequence encoding a pro-region of yeast α-mating factor. The more preferred embodiment of "A'" is an pro-region sequence of *Saccharomyces cerevisiae* α-mating factor (SEQ ID NO: 1).

In formula I of the present invention, parameter "B" represents sequence encoding a protein. In particular, the preferred embodiment is a secertory protein selected from those stated in the document entitled "Heterologous Proteins Expressed in *Pichia pastoris*." The more preferred embodiment is the protein denoted by S (Secreted) in comment column (mode, amount, signal sequence) of the same document. The further more preferred embodiment is protein denoted by S (Secreted) and α-MF in comment column (mode, amount, signal sequence) of the above mentioned document.

The further more preferred embodiment of the protein is a fungus secertory protein such as *Alternaria alternata* Alt a 1 allergen, *Alternaria alternata* rAlt a 2 allergen, *Aspergillus awamori* glucoamylase, *Aspergillus awamori* glucoamylase catalytic domain, *Aspergillus fumigatus* Asp f 2 allergen, *Aspergillus fumigatus* catalase L, *Aspergillus fumigatus* dipeptidyl peptidase IV (DPP IV), *Aspergillus fumigatus* dipeptidyl peptidase V (DPP V), *Aspergillus fumigatus* phytase, *Aspergillus giganteus* alpha-sarcin ribotoxin, *Aspergillus niger* β-glucosidase, *Aspergillus niger* phytase (phyA), *Candida guilliermondii* xylose reductase gene (xylI), *Aspergillus niger* endo-β-1,4-xylanase, *Candida rugosa* lipase 1 (CRL), *Fusarium solani* pectate lyase (pelC), *Fusarium solani* pectate lyase (pelD), *Geotrichum candidum* lipase isoenzymes, *Phytophthora cryptogea* β-cyptogein, *Rhizopus oryzae* lipase, *Saccharomyces cerevisiae* invertase, *Saccharomyces cerevisiae* Ktr1p, *Saccharomyces cerevisiae* (α-1,2-mannosyltransferase), *Schizophyllum commune* vitamin B2-aldehyde-forming enzyme, *Trametes versicolor* (white rot fungus) laccase (lccI), *Trichoderma harzianum* β-(1-6)-glucanase, *Candida albicans* MNT1 mannosyltransferase, *Candida antarctica* Lipase B, *Candida rugosa* LIP2 lipase, *Candida rugosa* lip4 lipase, *Kurtzmanomyces* sp. 1-11 lipase, *Metarhizium anisopliae* chymotrypsin, *Mucor pusillus* rennin, *Neurospora crassa* NOP-1, *Neocallimastix patriciarum* cellulase 6A-*Candida Antarctica* lipase B fusion protein, *Phanerochaete chrysosporium* glyoxal oxidase, *Phanerochaete chrysosporium* cellobiose dehydrogenase, *Phanerochaete chrysosporium* β-glucosidase, *Phaeseolus vulgaris* aspartic protease, Barley glucosidase, *Pleurotus sajor-caju* laccase isozyme, *Pycnoporus cinnabarinus* I-937 laccase, *Saccharomyces cerevisiae* Hsp70, *Saccharomyces cerevisiae* Kex 2p, *Trichodenna reesei* cellobiohydrolyase I, *Trichoderma reesei* cellobiohydrolyase Cel7A or *Trichodenna reesei* 1,2-α-kD-mannosidase.

The more particularly preferred embodiment of the protein is a secertory enzyme of fungus such as glucoamylase (GA) of *Rhizopus oryzae*, glucoamylase of *Aspergillus niger*, glucoamylase of *Aspergillus awamori*, glucoamylase catalytic domain of *Aspergillus awamori*, lipase of *Rhizopus oryzae*. In the most preferred embodiment of the protein is glucoamylase of *Rhizopus oryzae*.

In one embodiment of present invention, the parameter "n" in formula I represents 1-20. In the preferred embodiment, n is 2-10. In the more preferred embodiment, n is 3-7. In the most preferred embodiment, n is 7.

In one aspect, the present invention provides a vector which is capable of further positively regulating the protein yield in host cells which comprises sequence encoding Rab GTPase. In the preferred embodiment, the vector comprising the sequence encoding Rab GTPase selected from the group consisting of Sec3, Sec4, Sec5, Sec9, Sec15 and homologous thereof. In the most preferred embodiment, the vector comprising the sequence encoding Sec4 (SEQ ID NO: 13), which is cloned from genomic DNA of *Pichia pastoris*.

The present invention also provides a method for enhancing a protein production in *Pichia* comprising the steps of
(a) transforming *Pichia* with the expression vector of the invention; and
(b) expressing the protein in *Pichia*.

In the preferred protein produced by the above method is a secertory protein selected from those stated in the document entitled "Heterologous Proteins Expressed in *Pichia pastoris*." The more preferred embodiment is the protein denoted by S (Secreted) in comment column (mode, amount, signal sequence) of the same document. The further more preferred embodiment is protein denoted by S (Secreted) and α-MF in comment column (mode, amount, signal sequence) of the above mentioned document.

The further more preferred embodiment of the protein is a fungus secertory protein such as *Alternaria alternata* Alt a 1 allergen, *Alternaria alternata* rAlt a 2 allergen, *Aspergillus awamori* glucoamylase, *Aspergillus awamori* glucoamylase catalytic domain, *Aspergillus fumigatus* Asp f 2 allergen, *Aspergillus fumigatus* catalase L, *Aspergillus fumigatus* dipeptidyl peptidase IV (DPP IV), *Aspergillus fumigatus* dipeptidyl peptidase V (DPP V), *Aspergillus fumigatus* phytase, *Aspergillus giganteus* alpha-sarcin ribotoxin, *Aspergillus niger* β-glucosidase, *Aspergillus niger* phytase (phyA), *Candida guilliermondii* xylose reductase gene (xylI), *Aspergillus niger* endo-β-1,4-xylanase, *Candida rugosa* lipase 1 (CRL), *Fusarium solani* pectate lyase (pelC), *Fusarium solani* pectate lyase (pelD), *Geotrichum candidum* lipase isoenzymes, *Phytophthora cryptogea* β-cyptogein, *Rhizopus oryzae* lipase, *Saccharomyces cerevisiae* invertase, *Saccharomyces cerevisiae* Ktr1p, *Saccharomyces cerevisiae* (α-1,2-mannosyltransferase), *Schizophyllum commune* vitamin B2-aldehyde-forming enzyme, *Trametes versicolor* (white rot fungus) laccase (lccI), *Trichoderma harzianum* β-(1-6)-glucanase, *Candida albicans* MNT1 mannosyltransferase, *Candida antarctica* Lipase B, *Candida rugosa* LIP2 lipase, *Candida rugosa* lip4 lipase, *Kurtzmanomyces* sp. 1-11 lipase, *Metarhizium anisopliae* chymotrypsin, *Mucor pusillus* rennin, *Neurospora crassa* NOP-1, *Neocallimastix patriciarum* cellulase 6A-*Candida Antarctica* lipase B fusion protein, *Phanerochaete chrysosporium* glyoxal oxidase, *Phanerochaete chrysosporium* cellobiose dehydrogenase, *Phanerochaete chrysosporium* β-glucosidase, *Phaeseolus vulgaris* aspartic protease, Barley glucosidase, *Pleurotus sajor-caju* laccase isozyme, *Pycnoporus cinnabarinus* I-937 laccase, *Saccharomyces cerevisiae* Hsp70, *Saccharomyces cerevisiae* Kex 2p, *Trichoderma reesei* cellobiohydrolyase I, *Trichoderma reesei* cellobiohydrolyase Cel7A or *Trichoderma reesei* 1,2-α-kD-mannosidase.

Generally, the above method of the invention could increase protein production in 0.5-7, preferably 1.0-5, more preferably 1.5-3 folds.

The present invention will be described in detail below.

Construction Plasmids of Glucoamylase with Wild Type Signal Peptide and Modified Signal Peptide for *Pichia pastoris* Expression System The full-length cDNA encoding GA (SEQ ID NO: 12) of *R. oryzae* was provided by Simpson Biotech Co., Ltd., Taiwan., and amplified by PCR with the forward primer, 5' ROGA: 5'-TTCGAATTCATGCAATTATTCAATTTG-3' (SEQ ID NO: 7) and reverse primer, 3' ROGA: 5'-TTCGAATTCT-TAAGCGGCAGGTGCACC-3' (SEQ ID NO: 6). The PCR product was subcloned into yT&A TA cloning vector (Yeast Biotech Co., Ltd., Taiwan) to generate pT-WTSPGA (in designation of plasmid of glucoamylase with wild type signal peptide) plasmid. The MSPGA gene was constructed by two-stage PCR method. In the first stage, the pPICZαA plasmid, which contains the signal peptide of *Saccharomyces cerevisiae* α-mating factor (SEQ ID NO: 1), was used as a template to amplify the MSP fragment using primer pair 5'αSPαF: 5'-TTCGAATTCATGAAATTCTTCCTGCTGCTT CTCCTCATTGGATTCTGCTG GGCCGCTCCAGTCAA-CACT-3' (SEQ ID NO: 3) and 3' αFGA: 5'-ACTGCTAG-GAATACTTGCAGC TTCAGCCT CTCTTTT-3' (SEQ ID NO: 4).

The primer 5'αSPαF was designed to encode a 15 amino acid signal peptide of mouse salivary α-amylase with a mutation at the eighth residue (S8L point mutation as underlined) as well as the 5 amino acids, APVNT, in the pro-region of the signal peptide of *Saccharomyces cerevisiae* α-mating factor. The pT-WTSPGA plasmid was used as the second template to amplify the GA fragment by primer pair 5' αFGA: 5'-AAAA-GAGAGGCTGAAGCTGCAAGTATTCCTAGCAGT-3' (SEQ ID NO: 5) and 3' ROGA: 5'-TTCGAATTCTTAAGCG-GCAGGTGCACC-3' (SEQ ID NO: 6). In the second stage, MSP and GA fragments were both used as PCR templates to generate the MSPGA fragment by 5'αSPαF (SEQ ID NO: 3) and 3' ROGA (SEQ ID NO: 6) primers. The final PCR product was ligated into yT&A TA cloning vector to generate pT-MSPGA plasmid. The pT-WTSPGA and pT-MSPGA were digested with the restriction enzyme EcoRI and inserted into the same site of pPICZA to generate pPICZA-WTSPGA and pPICZA-MSPGA, respectively. The orientation and size of the insert DNA fragment in each clone was verified by DNA sequencing.

Transformation of *Pichia pastoris*

Transformation of *Pichia pastoris* was performed by lithium chloride method according to the manufacturer's protocol (Invitrogen). Ten micrograms of the recombinant plasmids pPICZA-WTSPGA and pPICZA-MSPGA were digested with PmeI to linearize each plasmid and transformed into *Pichia pastoris* GS115, respectively. *Pichia pastoris* transformants containing the desired insert were selected on YPD (1% yeast extract, 2% peptone, 2% dextrose and 2% agar) plates with 100 µg/ml zeocin (Invitrogen) for 3 days at 30° C.

Expression of GA in *Pichia pastoris*

*Pichia* transformants containing recombinant GA were grown in 10 ml BMGY (1% yeast extract, 2% peptone, 1.34% YNB, 0.4 mg/L biotin, 100 mM potassium phosphate at pH 6.0, and 1% glycerol) at 30° C. for 48 h with shaking at 200 rpm. The cells were harvested by centrifugation at 3000 g for 20 min at 25° C. and resuspended in BMMH (1.34% YNB, 0.4 mg/L biotin, 40 mg/L histidine, 100 mM potassium phosphate at pH 6.0, and 0.75% methanol) until the absorbance at $OD_{600}$ reached 40. The resuspended cells were cultured at 20° C. for 120 h with shaking at 200 rpm. For continuous induction, methanol was added to the culture medium to a final concentration of 0.75% every 24 hr. After 120 h, the cells were removed by centrifugation at 3000 g for 20 min at 4° C. and the culture supernatants were applied to 10% SDS-PAGE and assayed for GA activity.

Integration of SEC4 in Each MSPGA *Pichia* transformants

The sequence *Pichia pastoris* SEC4 has been disclosed. e.g., T. T. Huynh., et al., The genes of two G-proteins involved in protein transport in *Pichia pastoris*, Biochem. Biophys. Res. Commun. 280 (2001) 454-9T. Which was cloned from genomic DNA of *Pichia pastoris* by polymerase chain reaction (PCR) with the oligonucleotide primers 5'PpSEC4-E, 5'-TTGAATTCATGGCATCAAGAGGCACATCA-3' (SEQ ID NO:8) and 3'PpSEC4-E, 5'-TTGAATTCTCAACAACAAGACGATTTGGT-3' (SEQ ID NO:9). The PCR product was digested with EcoRI and ligated into EcoRI-digested pPIC3 to generate plasmid pPIC3-SEC4. *Pichia* transformants MSPGA-1, MSPGA-2, MSPGA-3 and MSPGA-7 were separately transformed with pPIC3 and pPIC3-SEC4 linearized by SalI digestion. The clones were selected on MD (0.67% yeast nitrogen base, $5 \times 10^{-4}$ biotin, 1% dextrose and 2% agar) plates and designated as MSPGA-1-pPIC3, MSPGA-2-pPIC3, MSPGA-3-pPIC3, MSPGA-7-pPIC3, MSPGA-1-SEC4, MSPGA-2-SEC4, MSPGA-3-SEC4 and MSPGA-7-SEC4, respectively.

EXAMPLES

Material, Strains, Vectors and Reagents

The *Pichia pastoris* strain GS115 (his4) and *Escherichia coli* strain TOP10F' were purchased from Invitrogen. TOP10' was used for plasmid DNA propagation and subcloning. The vectors pPICZαA, pPICZA and pPPC3 were from Invitrogen. Restriction endonucleases were from New England Biolabs, Inc. Polymerase EX-Taq and ligase were purchased from Takara. The synthetic oligonucleotide primers for PCR and sequencing were achieved from Mission BioTech. Culture media components were from Difco Laboratories.

Constructed Plasmids of Glucoamylase with Wild Type Signal Peptide and Modified Signal Peptide for *Pichia pastoris* Expression System The full-length cDNA encoding GA (SEQ ID NO: 12) of *R. oryzae* was provided by Simpson Biotech Co., Ltd. Taiwan. and amplified by PCR with the forward primer, 5' ROGA: 5'-TTCGAATTCATGCAATTATTCAATTTG-3' (SEQ ID NO: 7) and reverse primer, 3' ROGA: 5'-TTCGAATTCT-TAAGCGGCAGGTGCACC-3' (SEQ ID NO: 6). The PCR product was subcloned into yT&A TA cloning vector (Yeastern) to generate pT-WTSPGA (in designation of plasmid of glucoamylase with wild type signal peptide) plasmid. The MSPGA gene was constructed by two-stage PCR method. In the first stage, the pPICZαA plasmid, which contains the signal peptide of *Saccharomyces cerevisiae* α-mating factor (SEQ ID NO: 1), was used as a template to amplify the MSP fragment using primer pair 5'αSPαF: 5'-TTCGAATTCAT-GAAATTCTTCCTGCTGCTT C<u>T</u>CCTCATTGGATTCTGCTG GGCCGCTCCAGTCAA-CACT-3' (SEQ ID NO: 3) and 3' αFGA: 5'-ACTGCTAG-GAATACTTGCAGC TTCAGCCT CTCTTTT-3' (SEQ ID NO: 4). The primer 5'αSPαF was designed to encode a 15 amino acid signal peptide of mouse salivary α-amylase with a mutation at the eighth residue (S8L point mutation as underlined) as well as the 5 amino acids, APVNT, in the pro-region of the signal peptide of *Saccharomyces cerevisiae* α-mating factor. The pT-WTSPGA plasmid was used as the second template to amplify the GA fragment by primer pair 5'αFGA: 5'-AAAAGAGAGGCTGAAGCTGCAAGTATTC-CTAGCAGT-3' (SEQ ID NO: 5) and 3' ROGA: 5'-TTC-GAATTCTTAAGCGGCAGGTGCACC-3' (SEQ ID NO: 6). In the second stage, MSP and GA fragments were both used as PCR templates to generate the MSPGA fragment by 5'αSPαF (SEQ ID NO: 3) and 3' ROGA (SEQ ID NO: 6) primers. The final PCR product was ligated into yT&A TA cloning vector to generate pT-MSPGA plasmid. The pT-WTSPGA and pT-MSPGA were digested with the restriction enzyme EcoRI and inserted into the same site of pPICZA to generate pPICZA-WTSPGA and pPICZA-MSPGA, respectively. The orientation and size of the insert DNA fragment in each clone was verified by DNA sequencing.

Transformation of *Pichia pastoris*

Transformation of *Pichia pastoris* was performed by lithium chloride method according to the manufacturer's protocol (Invitrogen). Ten micrograms of the recombinant plasmids pPICZA-WTSPGA and pPICZA-MSPGA were digested with PmeI to linearize each plasmid and transformed into *Pichia pastoris* GS 115, respectively. *Pichia pastoris* transformants containing the desired insert were selected on YPD (1% yeast extract, 2% peptone, 2% dextrose and 2% agar) plates with 100 µg/ml zeocin (Invitrogen) for 3 days at 30° C.

Identification of *Pichia* Transformants Containing Multiple Copy Number of MSPGA Putative clones harbouring multiple copies of the inductive MSPGA expression cassette were selected using the Zeocin screening procedure. Zeocine resistant clones derived from the initial selection were streaked on YPD plates containing 0.1, 0.5, 1 and 2 mg/ml of Zeocine. After 4 days of incubation at 30° C., the growth ability of these clones was evaluated in the presence of increasing concentrations of the antibiotic.

The precise copy number of MSPGA in each clone was determined by Southern blotting analysis.

Genomic DNA Isolation

Ten milliliters saturated *Pichia pastoris* cultures in YPD were harvested by centrifugation at 3000 g for 20 min at 4° C. The pellet was washed in 10 ml water and collected by centrifugation at 3000 g for 20 min at 4° C. It was resuspended in 0.5 ml sterile water followed by addition of 0.2 ml lysis buffer containing 10 mM Tris-HCl, pH=8.0, 100 mM NaCl, 2% Triton X-100, 1% SDS and 1 mM EDTA, 0.3 g acid-washed glass beads (Sigma, G8772) and 0.2 ml phenol:chloroform:isoamylic alcohol (25:24:1). Lysis of cells was carried out by vigorous vortex at 25° C. for 3 min prior to addition of 0.2 ml Tris-EDTA buffer containing 10 mM Tris-HCl, 1 mM EDTA, pH=8.0. Proteins were extracted from aqueous phase with one volume of 24:1, v/v chloroform:isoamylic alcohol. The genomic DNA was precipitated with 1 ml 100% ethanol and resuspended in 0.4 ml Tris-EDTA buffer. The residual RNA was eliminated by incubation at 37° C. for 15 min in the presence of 75 μg/ml RNaseA (USB). The genomic DNA was precipitated again with 1 ml 100% ethanol in the presence of 0.04 M sodium acetate, pH5.2 and finally dissolved in 50 μl Tris-EDTA buffer.

Analysis of Genomic DNA From Different *Pichia* Integrant Clones WTSPGA and MSPGA Using Southern Blot Ten micrograms genomic DNA was digested with EcoRI at 37° C. for 16 h. The resulting fragments were separated by electrophoresis in a 0.8% agarose gel, transferred onto a Hybond-N nylon membrane (Amersham Biosciences) and hybridized with 32P-labeled probe. The probe specific for AOX1 promoter (AOX1P) was generated by PCR amplification using two primers, 5' AOX1P-probe 5'-GGGCTTGATTGGAGCTCGCTCATTC 3' (SEQ ID NO:10) and 3' AOX1P-probe 5'-CGTTTCGAATAATTAGTTGTTTTTT-3' (SEQ ID NO:11), followed by gel purification and $^{32}$P-labelling to give a 0.7 kb fragment $^{32}$P-AOX1P (ReadyPrime; Amersham Biosciences). Unincorporated label was removed before hybridization using a spin-50 mini-column (BioMax) according to the manufacturer's specification. The membrane was hybridized with the $^{32}$P-AOX1P at 42° C. for 16 h in hybridization buffer containing 50% v/v formamide, 6×SSC, 5×Denhard's solution, 0.5% w/v SDS, and 100 μg/ml denatured salmon sperm DNA. The membrane was further washed with 2×SSC/0.1% SDS for 10 min at 25° C. and 0.5×SSC/0.1% SDS for 10 min at 42° C. Autoradiograph was developed using Kodak X-ray film. Relative intensities of DNA blot were determined using a computing densitometer equipped with the ImageQuant analysis program (Amersham Biosciences).

Figure 2:
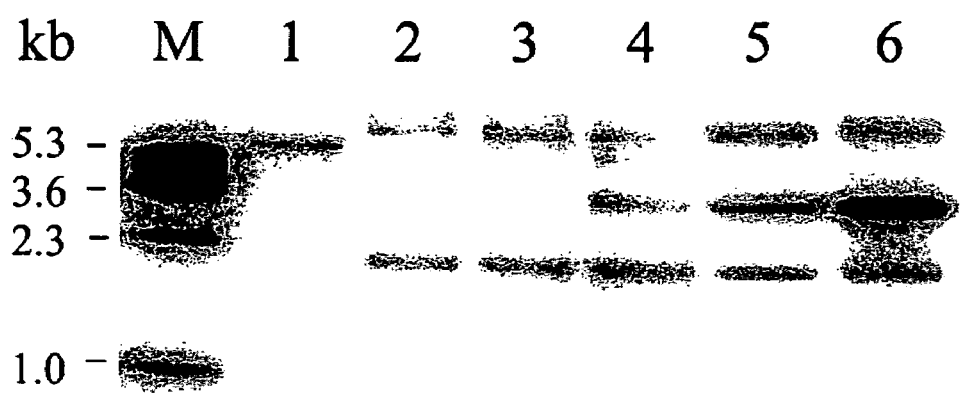
FIG. 2 is determination of copy number in *Pichia* transformants harboring WTSPGA and MSPGA. (A) Southern blotting analysis of genomic DNAs isolated from different *P. pastoris* integrant clones. Each genomic DNA was digested with EcoRI, separated by electrophoresis in a 0.8% agarose gel, and hybridized with $^{32}$P-AOX1P probe. Molecular weights of the size markers are shown on the left of the panel. Lanes M, marker; GS115; 2, WTSPGA-1; 3, MSPGA-1; 4, MSPGA-2; 5, MSPGA-3; and 6, MSPGA-7. (B) Integration of the GA expression cassette at AOX1 locus followed by linearization and single crossover insertion. Predicted structures and molecular events for GS115 (upper diagram), single copy transplacement (middle diagram), and multicopy transplacement (lower diagram). The arrows indicate the EcoRI site. Gray box, AOX1 gene; black box, AOX1 promoter (AOX1P); and white box, GA gene. n, gene copy number.
Figure 2:
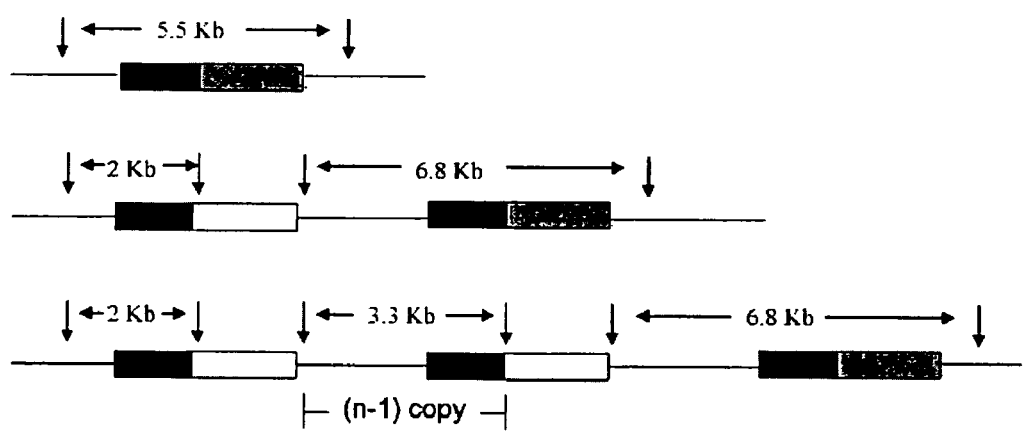

The Result of GA Secretion Employing Single Copy WTSPGA/*Pichia* and MSPGAl *Pichia* Transformants One harbored GA with wild type signal peptide (WTSP) contained 25 amino acids at the N-terminus. The other harbored GA fused with an N-terminal modified signal peptide (MSP) derived from the 15-aa signal peptide of the mouse salivary α-amylase followed by the 70 aa pro-region of the signal peptide of the *Saccharomyces cerevisiae* α-mating factor (SEQ ID NO:1). In addition, the eighth amino acid residue Ser was replaced with Leu in the MSP (FIG. 1). *Pichia pastoris* GS115 were transformed with the two expression plasmids pPICZA-WTSPGA and pPICZA-MSPGA by homologous recombination at chromosomal AOX1 promoter locus. Genomic DNA extracted from each *Pichia* transformant was digested with EcoRI, resolved on an agarose gel, and analyzed by Southern blotting with the $^{32}$P-AOX1P, a specific labeled probe. In GS115 host, this probe hybridized to a single band with a size of about 5.5 kb containing AOX1 gene (FIG. 2A lane 1). In *Pichia* transformants with a single copy of WTSPGA and MSPGA, the 5.5 kb fragment was disrupted by transforming DNA to give two bands of about 2.0 kb and 6.8 kb (FIG. 2A lanes 2 and 3). A diagram illustrating these recombinant constructs is shown in FIG. 2B (upper and middle). Based on the Southern blotting, we designated that the two *Pichia* transformants containing a single copy gene were WTSPGA-1 and MSPGA-1, respectively.

The Result of GA Secretion Employing Muticopy of MSPGA/*Pichia* Transformants

The high secretion level of GA upon fusing with MSP indicated that MSP was more efficient than WTSP as a functional signal peptide in the *Pichia* system. To verify whether recombinant *Pichia* with multi-copy MSPGA can further enhance the GA production, we screen for clones containing multiple copies of MSPGA inserts, the *Pichia* transformants were selected on plates with increasing concentration of Zeocin. The clones which tolerated higher Zeocin concentration appeared to possess high copy number of recombinant plasmid. Southern blotting analysis revealed that in to the 2.0 kb and 6.8 kb bands, all clones harboring multi-copy of MSPGA showed a single 3.3 kb band with differential intensities (FIG. 2A lanes 4, 5 and 6). Based on densitometric quantitation of Southern blotting With reference to the endogenous single copy 2 kb fragment, *Pichia* transformants with 2, 3 and 7 copies of MSPGA were identified and designated as MSPGA-2, MSPGA-3 and MSPGA-7, respectively (Table 1). A diagram shows MSPGA with multiple copy number (FIG. 2B lower). The phenotype of *Pichia* transformants were Mut$^+$ (data not shown).

TABLE 1

Determination of copy number of MSPGA in recombinant *Pichia* strains

| Lanes$^a$ | Intensity$^b$ of AOX1P 3.3 kb fragment | Intensity$^b$ of AOX1P 2 kb fragment | Ratio (3.3 kb fragment/2 kb fragment) | Calculated copy number |
|---|---|---|---|---|
| 4 | 189.7 | 218.4 | 0.869 | 2 |
| 5 | 406.9 | 232.6 | 1.749 | 3 |
| 6 | 1181 | 210.4 | 5.613 | 7 |

$^a$The lanes described in FIG. 2A
$^b$Intensity of DNA blot was determined using a computing densitometer equipped with the ImageQuant analysis program.

Expression of GA in *Pichia pastoris*

*Pichia* transformants containing recombinant GA were grown in 10 ml BMGY (1% yeast extract, 2% peptone, 1.34% YNB, 0.4 mg/L biotin, 100 mM potassium phosphate at pH 6.0, and 1% glycerol) at 30° C. for 48 h with shaking at 200 rpm. The cells were harvested by centrifugation at 3000 g for 20 min at 25° C. and resuspended in BMMH (1.34% YNB, 0.4 mg/L biotin, 40 mg/L histidine, 100 mM potassium phosphate at pH 6.0, and 0.75% methanol) until the absorbance at $OD_{600}$ reached 40. The resuspended cells were cultured at 20° C. for 120 h with shaking at 200 rpm. For continuous induction, methanol was added to the culture medium to a final concentration of 0.75% every 24 hr. After 120 h, the cells were removed by centrifugation at 3000 g for 20 min at 4° C. and the culture supernatants were applied to 10% SDS-PAGE and assayed for GA activity.

SDS-PAGE and Western Blot Analysis of the Expressed GA

Sodium dodecyl sulphate-polyacrylamide gel electrophoresis (SDS-PAGE) was carried out under reducing conditions with 10% running gels and 6% stacking gels. Twenty milliliters supernatant of the *Pichia* transformants cell culture was loaded into SDS-PAGE. The protein bands in the gel were detected by Coomassie brilliant blue staining and the gel were blotted onto a Hybond C nitrocellulose membrane (Amersham Biosciences). The immunoblotting was performed with anti-GA raised in a rabbit against the purified GA from *R. oryzae*. Immunoreactive bands were detected with anti-rabbit IgG-horseradish peroxidase conjugate in combination with ECL detection system (Amersham Biosciences).

Figure 3:
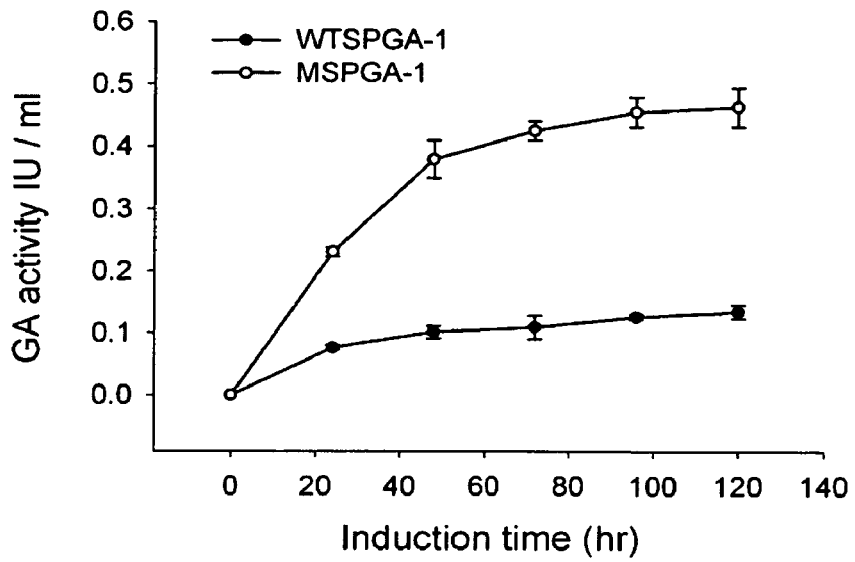
FIG. 3 represents GA secretion by WTSPGA-1 and MSPGA-1. (A) Time-dependent GA activity. Cultures were sampled at an intercal of 24 h and centrifuged to separate the cells from culture supernatant (extracellular fraction). The activity of GA secreted into the culture supernatant was detected by glucose assay kit. Error bars indicate standard deviation of the mean from three independent experiments. (B) Western Blot analysis of GA secretion level at 120 h. Twenty microliter culture supernatants of WTSPGA-1 and MSPGA-1 were loaded. The immunoblotting was performed with anti-GA raised in a rabbit of GA secretion in WTSPGA-1 and MSPGA-1 is quantified (lower panel).
Figure 3:
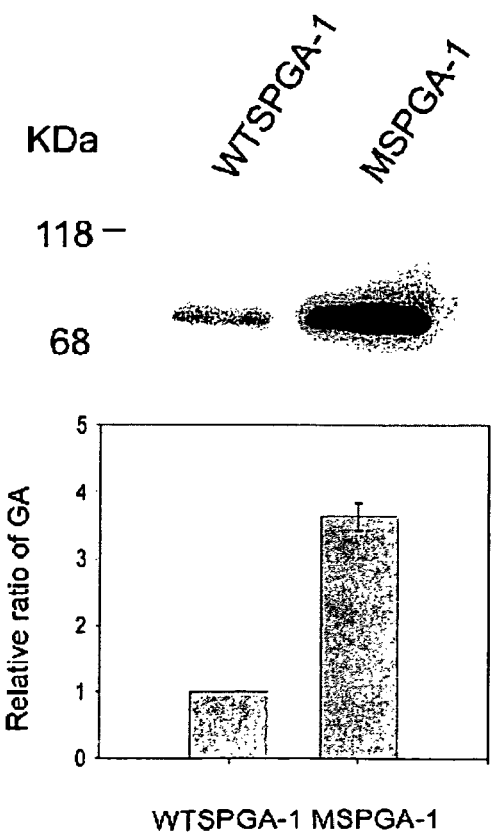

The result showed that the amount of secreted GA was in proportion to GA activity of WTSPGA-1 and MSPGA-1 (FIG. 3B). Therefore, *Pichia* transformant harboring a GA gene with MSP secreted 3.6 fold higher GA than that of original signal peptide.

The SDS-PAGE analysis further demonstrated a direct correlation between copy number and the secretion level of GA (FIG. 4B). As a result, the amount of GA secretion by MSPGA-7 were estimated to be about 56-fold as compared to WTSPGA-1. Accordingly, MSP and high copy number of the gene revealed a synergistic effect to improve secretory production of GA.

Activity Assay of the Expressed GA

GA activity was measured by using 0.5% soluble starch in 0.05 M NaOAc buffer, pH 4.5 at 37° C. The amount of glucose released from the starch digestion was determined using the glucose oxidase/peroxidase kit (Sigma, Lot: 96H9443). The supernatant of the yeast cell culture was collected by centrifugation at 3000 g for 20 min at 4° C. One hundred microliters of soluble starch and 100 µl of diluted supernatant were mixed and incubated at 37° C. for 5 min. Two hundred microliters assay kit reagent and 100 µl reaction solution were mixed and incubated at 37° C. for 5 min. Two hundred microliters of 12 N $H_2SO_4$ were added to stop the reaction, and the sample was measured at $O.D._{.540}$. One unit of GA activity was defined as the amount of enzyme releasing 1 µmol of glucose per one minute under the described conditions.

WTSPGA-1 and MSPGA-1 *Pichia* transformants containing a single copy of GA with different signal peptides were used to express GA (described in materials and methods). The supernatants were collected and assayed for their GA activities every 24 h. GA secretion increased rapidly up to 48 hr but gradually leveled off until 120 h. After cultivation for 120 h, the GA activity in the culture supernatants of transformed strains WTSPGA-1 and MSPGA-1 were measured to be 0.126 and 0.455 IU/ml, respectively (FIG. 3A).

The further effect of copy in each MSPGA/*Pichia* has been investigated; each *Pichia* transformant containing a known copy number of MSPGA was cultured to allow expression and secretion of GA under the same conditions. The GA activity in the culture medium of MSPGA-1, MSPGA-2, MSPGA-3 and MSPGA-7 were determined to be 0.455, 0.95, 1.664 and 7.042 IU/ml, respectively (FIG. 4A).

Integration of SEC4 in Each MSPGA *Pichia* Transformants

The sequence *Pichia pastoris* SEC4 has been disclosed. e.g., T. T. Huynh., et al., The genes of two G-proteins involved in protein transport in *Pichia pastoris*, Biochem. Biophys. Res. Commun. 280 (2001) 454-9T. Which was cloned from genomic DNA of *Pichia pastoris* by polymerase chain reaction (PCR) with the oligonucleotide primers 5'PpSEC4-E, 5'-TTGAATTCATGGCATCAAGAGGCACATCA-3' (SEQ ID NO: 8) and 3'PpSEC4-E, 5'-TTGAATTCTCAACAA-CAAGACGATTTGGT-3' (SEQ ID NO: 9). The PCR product was digested with EcoRI and ligated into EcoRI-digested pPIC3 to generate plasmid pPIC3-SEC4. *Pichia* transformants MSPGA-1, MSPGA-2, MSPGA-3 and MSPGA-7 were separately transformed with pPIC3 and pPIC3-SEC4 linearized by SalI digestion. The clones were selected on MD (0.67% yeast nitrogen base, $5 \times 10^{-4}$ biotin, 1% dextrose and 2% agar) plates and designated as MSPGA-1-pPIC3, MSPGA-2-pPIC3, MSPGA-3-pPIC3, MSPGA-7-pPIC3, MSPGA-1-SEC4, MSPGA-2-SEC4, MSPGA-3-SEC4 and MSPGA-7-SEC4, respectively.

Figure 5:
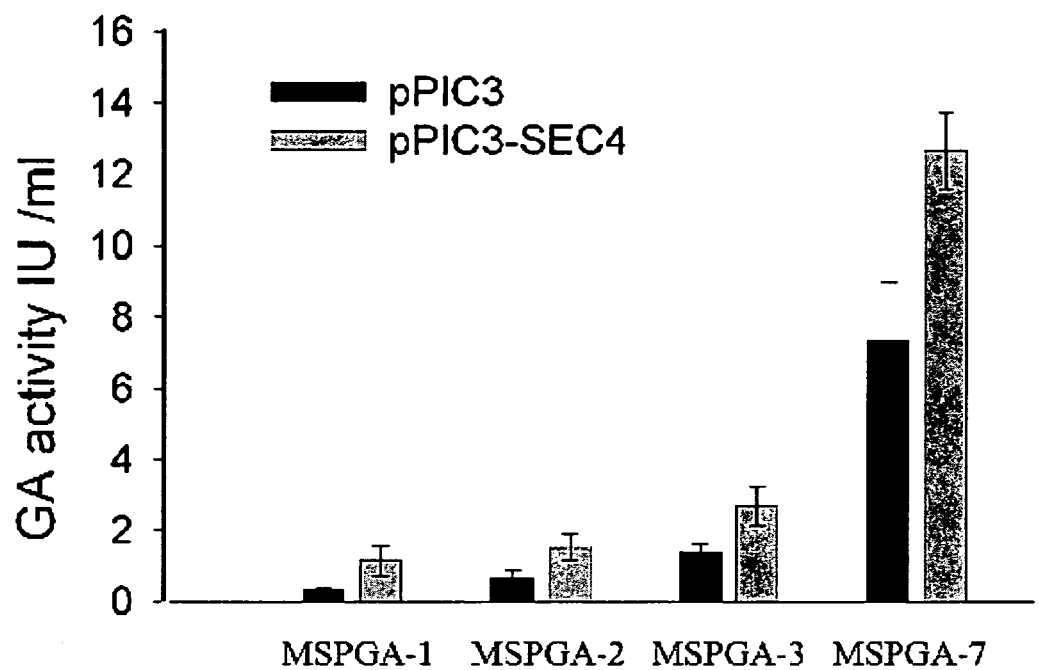
FIG. 5 represents improved GA secretion level by overexpression of SEC4. (A) Overexpression of SEC 4 in *P. pastoris* transformants containing various copy number of MSPGA inserts. All *P. pastoris* transformants were cultured in the same condition except for the addition of histidine. After 120 h of induction with 0.75% methanol, the activity of GA secreted into the culture supernatant was deviation of the mean from three independent experiments. (B) SDS-PAGE analysis of GA secretion level in *P. pastoris* transformants MSPGA-7-pPIC3 and MSPGA-7-SEC4 were loaded onto a 10% SDS-PAGE gel and detected by the coomassie brilliant blue staining.
Figure 5:
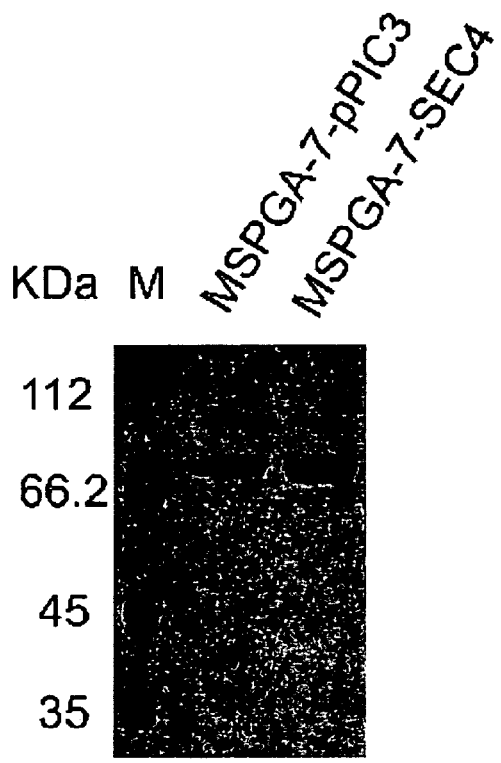

The effect of overexpressed Sec4p on GA secretion has been investigated; each *Pichia* transformant harboring MSPGA was further transformed with one copy of pPIC3-SEC4 at the chromosomal his4 locus and screened by Southern blotting (data not shown). Overexpression of SEC4 in each MSPGA/*Pichia* transformant was performed at the same condition as previously described except for the addition of histidine. It was found that the integration of a pPIC3 plasmid showed no influence on GA secretion in each MSPGA/*Pichia* transformant. The GA activity in the culture medium of MSPGA-1-SEC4, MSPGA-2-SEC4, MSPGA-3-SEC4 and MSPGA-7-SEC4 were measured to be 1.148, 1.518, 2.683 and 12.619 IU/ml, respectively (FIG. 5A). Hence, overexpression of SEC4 in our expression system harboring various copy number of MSPGA resulted in about 1.5 to 2.5-fold increase in production of secreted GA. SDS-PAGE analysis also revealed that MSPGA-7-SEC4 secreted approximately twice as much GA than MSPGA-7-pPIC3 (FIG. 5B). From these results, we found that overexpression of SEC4 enhanced the secretion level of GA in all MSPGA/*Pichia* transformants. Ultimately, the amount of secreted GA by MSPGA-7-SEC4 was up to 100-fold as compared to WTSPGA-1.

Purification of Recombinant GA

MSPGA-7-SEC4 transformant was grown in 200 ml BMGY at 30° C. for 48 h with shaking at 200 rpm. The cells were harvested by centrifugation at 3000 g for 20 min at 25° C. and resuspended in BMM until the absorbance at $OD_{600}$ reached 40. The resuspended cells were cultured at 20° C. with shaking at 200 rpm. For continuous induction of MSPGA-7-SEC4, a final concentration of 0.75% methanol was added to the culture medium every 24 hr. After 72 h incubation, the cells were removed by centrifugation at 3000 g for 20 min at 4° C. The recombinant GA in the supernatant was purified by FPLC cation exchange chromatography equipped with a HiTrap SP column (Amershame Pharmacia Quarry Bay). Elution was performed using a linear gradient of 0 to 1 M NaCl in 10 mM NaOAc, pH 5.5. The specific activity was calculated by using purified GA concentration determination by BCA protein assay kit (Pierce, Rockford, Ill., USA).

Discussion

Many genetic and environmental factors can influence the efficiency of a recombinant protein production in gene expression systems. As these factors are cross-regulated, it is of importance to optimize these involving variables in gene expression system of choice to achieve the highest yields. It found that the expression level of wild type R. oryzae GA when integrated into Pichia pastoris chromosome as a single copy gene was lower than that reported for methylotrophic yeast Candida boidinii. e.g., Y Sakai., et al., High-level secretion of fungal glucoamylase using the Candida boidinii gene expression system, Biochim. Biophys. Acta. 1308 (1996) 81-7. The feasibility of improving an expression system for GA secretion in Pichia pastoris by a certain measure depends on whether several steps of protein processing are reaching to their limit.

Figure 4:
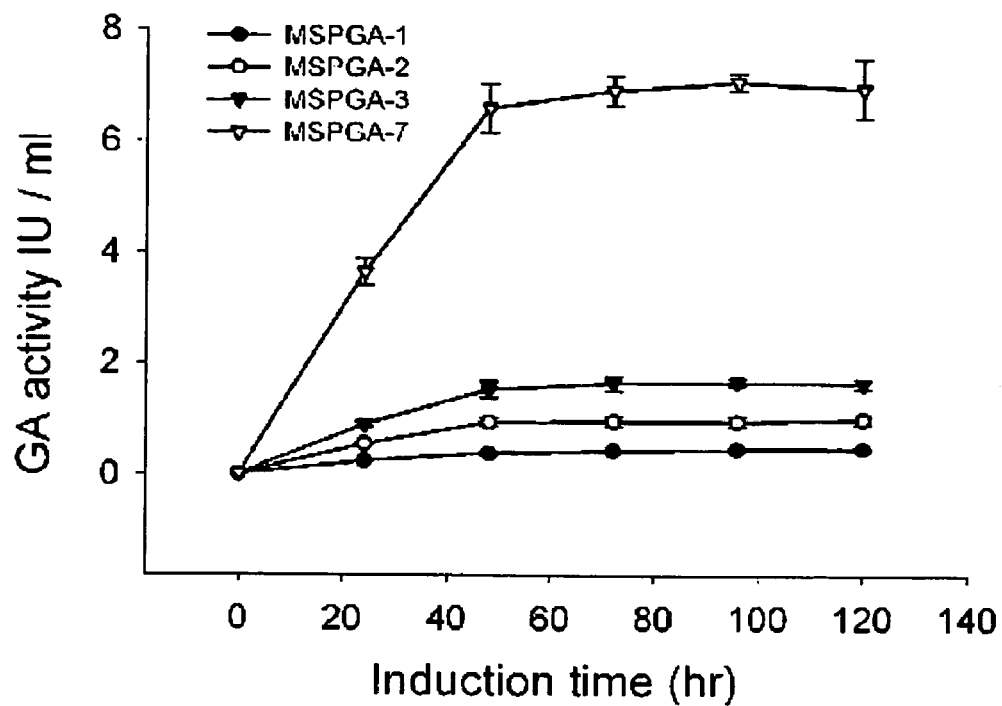
FIG. 4 represents the enhancement of GA secretion in *Pichia* transformants containing different copy number of MSPGA. (A) Time course of GA activity in *P. pastoris* transformants containing various copy number of MSPGA inserts. Cultures were sampled at an interval of 24 h and centrifuged to separate the cells from culture supernatant (extracellular fraction). The activity of GA secreted into the culture supernatant was assayed by glucose assay kit. Error bars indicate standard deviation of the mean from three independent experiments. (B) SDS-PAGE analysis of GA secretion level at 120 h. Twenty microliter culture supernatants of GS115, MSPGA-1, MSPGA-2, MSPGA-3, and MSPGA-7 were loaded onto a 10% SDS-PAGE gel and detected by the Coomassie brilliant blue staining.
Figure 4:
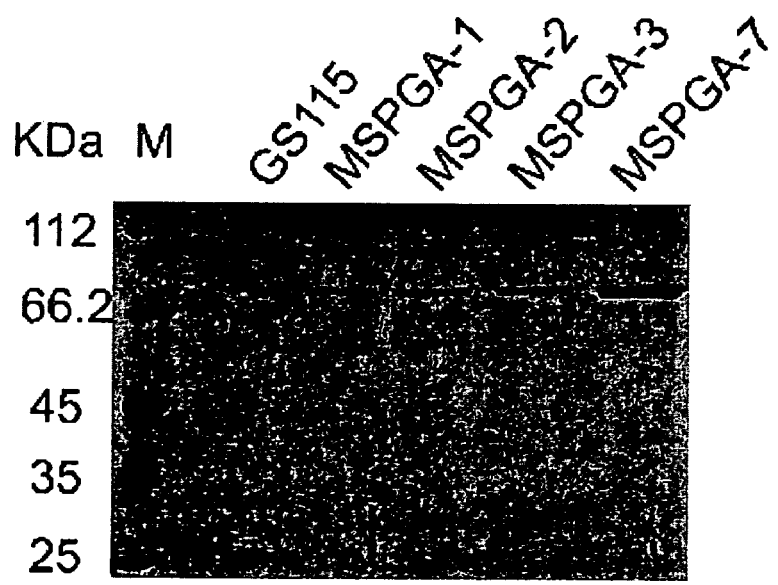

It is well documented that the conformation of the signal peptide is one of the important factors for its function. One of the distinguishing features of signal peptide is the hydrophobic region which usually forms an α-helical conformation e.g., G. von Heijne., Signal sequences. The limits of variation, J. Mol. Biol. 184 (1985) 99-105. To improve the hydrophobicity of the signal peptide of mouse salivary α-amylase, the eighth amino acid residue Ser was substituted with Leu. In addition, previous studies have indicated that the pro-signal peptide of Saccharomyces cerevisiae α-mating factor (SEQ ID NO:1) increased the secretion of human lysozyme in Pichia pastoris. C. Oka, M., et al., Human lysozyme secretion increased by alpha-factor pro-sequence in Pichia pastoris, Biosci. Biotechnol. Biochem. 63 (1999) 1977-83. and the position of the N-linked oligosaccharide chain on the alpha-factor pro-peptide was further demonstrated to be important for facilitating efficient secretion e.g., T. Kjeldsen., et al., alpha-Factor pro-peptide N-linked oligosaccharides facilitate secretion of the insulin precursor in Saccharomyces cerevisiae, Biotechnol. Appl. Biochem. 27 (Pt 2) (1998) 109-15. Thus, MSP was used to replace WTSP as the leader sequence for expression of R. oryzae GA in Pichia pastoris. The clone with one copy of insert MSPGA-1 showed 3.6-fold increase in GA secretion as compared to that of WTSPGA-1 confirming that the MSP was more efficient than WTSP on GA secretion in Pichia pastoris. Subsequently, the copy number of MSPGA inserts and its correlation with GA secretion were examined. Since it has been reported that the increase in copy number of the expression cassette was effective up to a certain protein level, see e.g., A. Vassileva., et al., Expression of hepatitis B surface antigen in the methylotrophic yeast Pichia pastoris using the GAP promoter, J. Biotechnol. 88 (2001) 21-35; J. H. Lipschutz., et al., Exocytosis: the many masters of the exocyst, Curr. Biol. 12 (2002) R212-4. Recombinant clones with different copy number of MSPGA in Pichia pastoris was screened. A direct correlation between copy number and the secretion level of GA by Pichia transformants was observed as shown in FIG. 4. As a result, the MSPGA-7 demonstrated higher GA secretion levels up to 56-fold as compared to WTSPGA-1.

The involvement of Sec4p on GA secretion in Pichia pastoris was further investigated. It demonstrated that overexpression of SEC4 in Pichia transformants containing different copy number of MSPGA enhanced the GA secretion level about 1.5 to 2.5-fold. Sec4p plays a central role in exocytosis. It is one member of eleven Ypt/Rab-GTPases that share characteristic features and are involved in vesicular transport in Saccharomyces cerevisiae, e.g., T. Lazar., et al., Vesicular transport: how many Ypt/Rab-GTPases make a eukaryotic cell?, Trends Biochem. Sci. 22 (1997) 468-72. and previous study indicated that overexpression of SEC4 resulted in increased production of secreted α-amylase in Saccharomyces cerevisiae. e.g., J. H. Toikkanen., et al., The beta subunit of the Sec61p endoplasmic reticulum translocon interacts with the exocyst complex in Saccharomyces cerevisiae, J. Biol. Chem. 278 (2003) 20946-53. In the present data, it found that overexpressed Sec4p improved secretion level of GA in Pichia pastoris and further support the functional conservation of the machinery required for vesicular traffic. Finally, the MSPGA-7-SEC4 showed a 100-fold secretion level of GA as compared to WTSPGA-1. Given the above, the invention demonstrated the R. oryzae GA secretion in Pichia pastoris from 3.085 μg to 308.986 μg in 1 ml of culture medium. A complete comparison of GA production in all Pichia transformants constructed in this research is illustrated in Table 2.

Pichia pastoris SEC4 was first cloned and characterized by Trang et al in 2001, e.g., T. T. Huynh., et al., The genes of two G-proteins involved in protein transport in Pichia pastoris, Biochem. Biophys. Res. Commun. 280 (2001) 454-9. but its physiological effects was rarely discussed. The present invention demonstrated that overexpression of SEC4 enhanced GA secretion in all MSPGA/Pichia transformants. In conclusion, the combination of modified signal peptide, high copy number of the gene, and overexpressed Sec4p could successfully secret R. oryzae GA from 1 to 100-fold in Pichia pastoris. The optimal GA secretion level shows up to about 300 μg in 1 ml of culture medium. In addition, overexpression of SEC4 in Pichia pastoris with high cell density was demonstrated to improve heterologus protein secretion.

TABLE 2

Comparison of GA production in Pichia transformants

|  | WTSP GA-1 | MSPG A-1 | MSPG A-2 | MSPG A-3 | MSPG A-7 | MSPG A-1-SE C4 | MSPG A-2-SE C4 | MSPG A-3-SE C4 | MSPG A-7-SE C4 |
|---|---|---|---|---|---|---|---|---|---|
| IU/ml[a] | 0.126 | 0.455 | 0.95 | 1.664 | 7.042 | 1.148 | 1.518 | 2.683 | 12.619 |
| µg/ml[b] | 3.085 | 11.141 | 23.262 | 40.744 | 172.429 | 28.109 | 37.269 | 65.695 | 308.986 |
| Fold of enhancement[c] | 1 | 3.605 | 7.54 | 13.2 | 55.89 | 9.111 | 12.048 | 21.293 | 100.151 |

[a]One unit activity of GA is defined as the amount of enzyme that liberates 1 µmol of glucose per minute in 1 ml of culture medium.
[b]GA (µg/ml) based on specific activity of 40.84 U/mg protein.
[c]The folds of enhancement relative to WTSPGA-1.

What is claimed is:

1. A nucleic acid molecule comprising a nucleic acid sequence for mediating gene expression, protein expression, and protein secretion, wherein the nucleic acid sequence comprises a sequence encoding a secretory protein, the nucleic acid sequence having a formula:

$[A(A')_x B]_n$ wherein A represents a sequence encoding a promoter operably linked to a sequence encoding a signal peptide; A' represents a sequence encoding a pro-region of yeast α-mating factor (SEQ ID NO: 1); B represents the sequence encoding the secretory protein; x represents 0-1; n represents 1-20; provided that if x is 0 then n is not 1; wherein the sequence encoding the signal peptide, SEQ ID NO:1 and the sequence encoding the secretory protein are operably linked and under control of the promoter, said signal peptide is selected from a modified signal peptide of α-amylase, wherein Serine at position 8 of the signal peptide of α-amylase is replaced by Leucine (SEQ ID NO: 15) or a modification of SEQ ID NO:15 wherein position 8 comprises an amino acid selected from Isoleucine, Valine, Alanine, Glycine or Phenylalanine; and said protein is *Alternaria alternata* Alt a 1 allergen, *Alternaria alternata* rAlt a 2 allergen, *Aspergillus awamori* glucoamylase, *Aspergillus awamori* glucoamylase catalytic domain, *Aspergillus fumigatus* Asp f 2 allergen, *Aspergillus fumigatus* catalase L, *Aspergillus fumigatus* dipeptidyl peptidase IV (DPP IV), *Aspergillus fumigatus* dipeptidyl peptidase V (DPP V), *Aspergillus fumigatus* phytase, *Aspergillus giganteus* alpha-sarcin ribotoxin, *Aspergillus niger* 13-glucosidase, *Aspergillus niger* phytase (phyA), *Candida guilliermondii* xylose reductase gene (xylI), *Aspergillus niger* endo-β-1,4-xylanase, *Candida rugosa* lipase 1 (CRL), *Fusarium solani* pectate lyase (pelC), *Fusarium solani* pectate lyase (pelD), *Geotrichum candidum* lipase isoenzymes, *Phytophthora cryptogea* β-cyptogein, *Rhizopus oryzae* lipase, *Saccharomyces cerevisiae* invertase, *Saccharomyces cerevisiae* Ktr1p, *Saccharomyces cerevisiae* (a-1,2-mannosyltransferase), *Schizophyllum commune* vitamin B2-aldehyde-forming enzyme, *Trametes versicolor* (white rot fungus) laccase (lccI), *Trichoderma harzianum* β-(1-6)-glucanase, *Candida albicans* MNT1 mannosyltransferase, *Candida antarctica* Lipase B, *Candida rugosa* LIP2 lipase, *Candida rugosa* lip4 lipase, *Kurtzmanomyces* sp. 1-11 lipase, *Metarhizium anisopliae* chymotrypsin, *Mucor pusillus* rennin, *Neurospora crassa* NOP-1, *Neocallimastix patriciarum* cellulase 6A-*Candida Antarctica* lipase B fusion protein, *Phanerochaete chrysosporium* glyoxal oxidase, *Phanerochaete chrysosporium* cellobiose dehydrogenase, *Phanerochaete chrysosporium* β-glucosidase, *Phaeseolus vulgaris* aspartic protease, Barley glucosidase, *Pleurotus sajor-caju* laccase isozyme, *Pycnoporus cinnabarinus* 1-937 laccase, *Saccharomyces cerevisiae* Hsp70, *Saccharomyces cerevisiae* Kex 2p, *Trichoderma reesei* cellobiohydrolyase I, *Trichoderma reesei* cellobiohydrolyase Cel7A or *Trichoderma reesei* 1,2-a-kD-mannosidase.

2. The nucleic acid molecule of claim 1, wherein n is 7.

* * * * *

SEQUENCE LISTING

<160> NUMBER OF SEQ ID NOS: 16

<210> SEQ ID NO 1
<211> LENGTH: 498
<212> TYPE: DNA
<213> ORGANISM: Saccharomyces cerevisiae

<400> SEQUENCE: 1

```
atgagatttc cttcaatttt tactgcagtt ttattcgcag catcctccgc attagctgct     60
ccagtcaaca ctacaacaga agatgaaacg gcacaaattc cggctgaagc tgtcatcggt    120
tacttagatt tagaagggga tttcgatgtt gctgttttgc cattttccaa cagcacaaat    180
aacgggttat tgtttataaa tactactatt gccagcattg ctgctaaaga agaaggggta    240
tctttggata aaagagaggc tgaagcttgg cattggttgc aactaaaacc tggccaacca    300
atgtacaaga gagaagccga agctgaagct tggcattggc tgcaactaaa gcctggccaa    360
ccaatgtaca aagagaagc cgacgctgaa gcttggcatt ggctgcaact aaagcctggc    420
caaccaatgt acaaaagaga agccgacgct gaagcttggc attggttgca gttaaaaccc    480
ggccaaccaa tgtactaa                                                 498
```

<210> SEQ ID NO 2
<211> LENGTH: 4568
<212> TYPE: DNA
<213> ORGANISM: Artificial Sequence
<220> FEATURE:
<223> OTHER INFORMATION: pT-WTSPGA plasmid

<400> SEQUENCE: 2

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gtaatacgac tcactatagg    420
gcgagctcgg tacccggggcg aattccaagc ttgaatctat gcaactgttc aatttgccat    480
tgaaagtttc attctttctc gtcctctctt acttttcttt gctcgttcct gctgcaagca    540
ttcctagtag tgcttctgtc cagcttgatt catacaatta cgatggctct acttttcag    600
```

```
gaaaaattta tgtcaagaac attgcttact ccaagaaggt tactgtaatt tacgccgatg    660
gctctgacaa ctggaataat aatggaaaca ccattgctgc ttcttactct gctcctattt    720
ctggatcaaa ttacgaatac tggacattct ctgcctccat taatggtatc aaggagttct    780
acattaagta tgaggtcagt ggaaaaacat actatgataa caacaattct gccaattacc    840
aagtatctac atccaagcct actactacta ctgctactgc tactactact accgctcctt    900
ccacttcaac cacgactccc ccctcaaggt ctgagccagc tactttccca actggtaact    960
ctacaatctc ctcatggatt aagaagcaag aaggtatcag ccgctttgct atgcttcgaa   1020
acatcaatcc tcctggaagc gctaccggtt tcattgctgc ctcactctct accgctggtc   1080
ccgattacta ctatgcttgg actcgtgatg ctgcattaac ctccaatgta attgtttacg   1140
aatacaaacac tactttgtcc ggtaataaga ctatcctcaa cgtcctcaag gactatgtta   1200
cattctcagt caagacccaa tcaacttcta ccgtctgtaa ctgccttggt gagcctaagt   1260
tcaatcctga tgcttctggc tatactggtg cttgggaag acctcaaaat gatggacctg   1320
ctgaacgtgc tactaccttc attttgtttg ctgacagtta tcttactcaa acaaaggatg   1380
cttcctatgt cactggtaca ctcaagcctg ctatcttcaa ggacttggac tatgtcgtca   1440
atgtctggtc taatggctgt ttcgatttat gggaagaagt caacggtgtt cacttctata   1500
ctttaatggt tatgcgtaag ggtttgcttc ttggtgcaga tttcgctaaa cgtaacggtg   1560
actctactcg tgcatctacc tatagcagca ctgcatccac tattgcaaac aagatctcta   1620
gcttctgggt ttcttctaat aactggattc aagtcagtca aagcgttact ggtggtgtca   1680
gtaaaaaggg tttggatgtc tccacattgt tggctgctaa ccttggtagt gttgatgatg   1740
gattcttcac tcctggctct gaaaagatcc ttgccactgc tgttgctgtt gaagactcct   1800
tcgcttcctt gtatcctatc aacaaaaacc ttccatctta ccttggtaac tctattggta   1860
gatatcctga agacacttac aatggtaacg gaaactctca aggaaactct tggttcttgg   1920
ctgtaactgg ttacgctgag ctctattacc gtgccatcaa ggaatggatc ggcaacggtg   1980
gtgtcactgt cagcagcata agtttaccct tcttcaagaa gtttgattca tctgctacat   2040
ctggaaagaa gtacactgtt ggtacctccg actttaacaa ccttgctcaa aatattgcac   2100
tcgctgctga ccgtttcttg tccactgtcc agctccatgc tcacaacaat ggatctcttg   2160
ctgaagagtt tgaccgcacc actggtttat ccaccggtgc tagagacttg acctggtctc   2220
acgcttcttt aatcaccgct tcttacgcta aggctggtgc acctgccgct taaggtgtga   2280
attcgaattc agatctggat cccctctaga gtcgacctgc aggcatgcaa gcttggcgta   2340
atcatggtca tagctgtttc ctgtgtgaaa ttgttatccg ctcacaattc cacacaacat   2400
acgagccgga agcataaagt gtaaagcctg gggtgcctaa tgagtgagct aactcacatt   2460
aattgcgttg cgctcactgc ccgctttcca gtcgggaaac ctgtcgtgcc agctgcatta   2520
atgaatcggc caacgcgcgg ggagaggcgg tttgcgtatt gggcgctctt ccgcttcctc   2580
gctcactgac tcgctgcgct cggtcgttcg ctgcggcga gcggtatcag ctcactcaaa    2640
ggcggtaata cggttatcca cagaatcagg ggataacgca ggaaagaaca tgtgagcaaa   2700
aggccagcaa aaggccagga accgtaaaaa ggccgcgttg ctggcgtttt tccataggct   2760
ccgcccccct gacgagcatc acaaaaatcg acgctcaagt cagaggtggc gaaacccgac   2820
aggactataa agataccagg cgtttccccc tggaagctcc ctcgtgcgct ctcctgttcc   2880
gaccctgccg cttaccggat acctgtccgc ctttctccct tcgggaagcg tggcgctttc   2940
tcatagctca cgctgtaggt atctcagttc ggtgtaggtc gttcgctcca agctgggctg   3000
```

```
tgtgcacgaa ccccccgttc agcccgaccg ctgcgcctta tccggtaact atcgtcttga    3060
gtccaacccg gtaagacacg acttatcgcc actggcagca gccactggta acaggattag    3120
cagagcgagg tatgtaggcg gtgctacaga gttcttgaag tggtggccta actacggcta    3180
cactagaagg acagtatttg gtatctgcgc tctgctgaag ccagttacct tcggaaaaag    3240
agttggtagc tcttgatccg gcaaacaaac caccgctggt agcggtggtt tttttgtttg    3300
caagcagcag attacgcgca gaaaaaaagg atctcaagaa gatcctttga tcttttctac    3360
ggggtctgac gctcagtgga acgaaaactc acgttaaggg attttggtca tgagattatc    3420
aaaaaggatc ttcacctaga tccttttaaa ttaaaaatga agttttaaat caatctaaag    3480
tatatatgag taaacttggt ctgacagtta ccaatgctta atcagtgagg cacctatctc    3540
agcgatctgt ctatttcgtt catccatagt tgcctgactc cccgtcgtgt agataactac    3600
gatacgggag ggcttaccat ctggccccag tgctgcaatg ataccgcgag acccacgctc    3660
accggctcca gatttatcag caataaacca gccagccgga agggccgagc gcagaagtgg    3720
tcctgcaact ttatccgcct ccatccagtc tattaattgt tgccgggaag ctagagtaag    3780
tagttcgcca gttaatagtt tgcgcaacgt tgttgccatt gctacaggca tcgtggtgtc    3840
acgctcgtcg tttggtatgg cttcattcag ctccggttcc caacgatcaa ggcgagttac    3900
atgatccccc atgttgtgca aaaaagcggt tagctccttc ggtcctccga tcgttgtcag    3960
aagtaagttg gccgcagtgt tatcactcat ggttatggca gcactgcata attctcttac    4020
tgtcatgcca tccgtaagat gcttttctgt gactggtgag tactcaacca agtcattctg    4080
agaatagtgt atgcggcgac cgagttgctc ttgcccggcg tcaatacggg ataataccgc    4140
gccacatagc agaactttaa aagtgctcat cattggaaaa cgttcttcgg ggcgaaaact    4200
ctcaaggatc ttaccgctgt tgagatccag ttcgatgtaa cccactcgtg cacccaactg    4260
atcttcagca tctttttactt tcaccagcgt ttctgggtga gcaaaaacag gaaggcaaaa    4320
tgccgcaaaa aagggaataa gggcgacacg gaaatgttga atactcatac tcttcctttt    4380
tcaatattat tgaagcattt atcagggtta ttgtctcatg agcggataca tatttgaatg    4440
tatttagaaa aataaacaaa tagggggttcc gcgcacattt ccccgaaaag tgccacctga    4500
cgtctaagaa accattatta tcatgacatt aacctataaa aataggcgta tcacgaggcc    4560
ctttcgtc                                                             4568

<210> SEQ ID NO 3
<211> LENGTH: 69
<212> TYPE: DNA
<213> ORGANISM: Artificial Sequence
<220> FEATURE:
<223> OTHER INFORMATION: primer 5'-alpha-SP-alpha-F

<400> SEQUENCE: 3
ttcgaattca tgaaattctt cctgctgctt ctcctcattg gattctgctg ggccgctcca    60
gtcaacact                                                             69

<210> SEQ ID NO 4
<211> LENGTH: 36
<212> TYPE: DNA
<213> ORGANISM: Artificial Sequence
<220> FEATURE:
<223> OTHER INFORMATION: primer 3' alpha-FGA

<400> SEQUENCE: 4
```
actgctagga atacttgcag cttcagcctc tctttt                                36

<210> SEQ ID NO 5
<211> LENGTH: 36
<212> TYPE: DNA
<213> ORGANISM: Artificial Sequence
<220> FEATURE:
<223> OTHER INFORMATION: primer 5' alpha-FGA

<400> SEQUENCE: 5
aaaagagagg ctgaagctgc aagtattcct agcagt                                36

<210> SEQ ID NO 6
<211> LENGTH: 27
<212> TYPE: DNA
<213> ORGANISM: Artificial Sequence
<220> FEATURE:
<223> OTHER INFORMATION: primer 3'ROGA

<400> SEQUENCE: 6
ttcgaattct taagcggcag gtgcacc                                          27

<210> SEQ ID NO 7
<211> LENGTH: 27
<212> TYPE: DNA
<213> ORGANISM: Artificial Sequence
<220> FEATURE:
<223> OTHER INFORMATION: primer 5'ROGA

<400> SEQUENCE: 7
ttcgaattca tgcaattatt caatttg                                          27

<210> SEQ ID NO 8
<211> LENGTH: 29
<212> TYPE: DNA
<213> ORGANISM: Artificial Sequence
<220> FEATURE:
<223> OTHER INFORMATION: primer 5'PpSEC4-E

<400> SEQUENCE: 8
ttgaattcat ggcatcaaga ggcacatca                                        29

<210> SEQ ID NO 9
<211> LENGTH: 29
<212> TYPE: DNA
<213> ORGANISM: Artificial Sequence
<220> FEATURE:
<223> OTHER INFORMATION: primer 3'PpSEC4-E

<400> SEQUENCE: 9
ttgaattctc aacaacaaga cgatttggt                                        29

<210> SEQ ID NO 10
<211> LENGTH: 25
<212> TYPE: DNA
<213> ORGANISM: Artificial Sequence
<220> FEATURE:
<223> OTHER INFORMATION: 5'AOX1P-probe

<400> SEQUENCE: 10
gggcttgatt ggagctcgct cattc                                            25

<210> SEQ ID NO 11
<211> LENGTH: 25
<212> TYPE: DNA
<213> ORGANISM: Artificial Sequence

```
<220> FEATURE:
<223> OTHER INFORMATION: 3'AOX1P-probe

<400> SEQUENCE: 11
cgtttcgaat aattagttgt ttttt                                              25

<210> SEQ ID NO 12
<211> LENGTH: 1815
<212> TYPE: DNA
<213> ORGANISM: Rhizopus oryzae

<400> SEQUENCE: 12
atgcaactgt tcaatttgcc attgaaagtt tcattctttc tcgtcctctc ttacttttct        60
ttgctcgttt ctgctgcaag cattcctagt agtgcttctg tccagcttga ttcatacaat       120
tacgatggct ctacttttc aggaaaaatt tatgtcaaga acattgctta ctccaagaag        180
gttactgtaa tttacgccga tggctctgac aactggaata taatggaaa caccattgct        240 gcttcttact ctgctcctat ttctggatca aattacgaat actggacatt tctgcctcc        300 attaatggta tcaaggagtt ctacattaag tatgaggtca gtggaaaaac atactatgat       360
aacaacaatt ctgccaatta ccaagtatct acatccaagc ctactactac tactgctact      420
gctactacta ctaccgctcc ttccacttca accacgactc cccctcaag gtctgagcca       480 gctactttcc caactggtaa ctctacaatc tcctcatgga ttaagaagca agaaggtatc      540
agccgctttg ctatgcttcg aaacatcaat cctcctggaa gcgctaccgg tttcattgct      600
gcctcactct ctaccgctgg tcccgattac tactatgctt ggactcgtga tgctgcatta     660
acctccaatg taattgttta cgaatacaac actactttgt ccggtaataa gactatcctc     720
aacgtcctca aggactatgt tacattctca gtcaagaccc aatcaacttc taccgtctgt    780
aactgccttg gtgagcctaa gttcaatcct gatgcttctg ctatactgg tgcttgggga      840 agacctcaaa atgatggacc tgctgaacgt gctactacct tcatttttgtt tgctgacagt    900 tatcttactc aaacaaagga tgcttcctat gtcactggta cactcaagcc tgctatcttc    960
aaggacttgg actatgtcgt caatgtctgg tctaatggct gtttcgattt atgggaagaa   1020
gtcaacggtg ttcacttcta tactttaatg gttatgcgta agggtttgct tcttggtgca    1080
gatttcgcta acgtaacgg tgactctact cgtgcatcta cctatagcag cactgcatcc    1140
actattgcaa caagatctc tagcttctgg gtttcttcta ataactggat tcaagtcagt     1200
caaagcgtta ctggtggtgt cagtaaaaag ggtttggatg tctccacatt gttggctgct    1260
aaccttggta gtgttgatga tggattcttc actcctggct ctgaaaagat ccttgccact   1320
gctgttgctg ttgaagactc cttcgcttcc ttgtatccta tcaacaaaaa ccttccatct   1380
taccttggta actctattgg tagatatcct gaagacactt acaatggtaa cggaaactct   1440
caaggaaact cttggttctt ggctgtaact ggttacgctg agctctatta ccgtgccatc   1500
aaggaatgga tcggcaacgg tggtgtcact gtcagcagca taagtttacc cttcttcaag  1560
aagtttgatt catctgctac atctggaaag aagtacactg ttggtacctc cgactttaac   1620
aaccttgctc aaaatattgc actcgctgct gaccgtttct tgtccactgt ccagctccat   1680
gctcacaaca atggatctct tgctgaagag tttgaccgca ccactggttt atccaccggt    1740
gctagagact tgacctggtc tcacgcttct ttaatcaccg cttcttacgc taaggctggt   1800
gcacctgccg cttaa                                                    1815

<210> SEQ ID NO 13
```

```
<211> LENGTH: 615
<212> TYPE: DNA
<213> ORGANISM: Pichia pastoris

<400> SEQUENCE: 13
atggcatcaa gaggcacatc aaggcaacag tatgacctca ctatgaagct attgctagta      60
ggagactctg gtgtaggaaa gtcctgtctt ttattgagat tgtggacga ctcgttcaac     120 ccttccttca tcactactat tggtattgac tttaagattc gaaccgtgga gatcaatgga     180
aagaaagtca agctgcaaat ttgggatacc gctggccaag agagattcag aactattact     240
actgcctact acagaggggc catgggtatc atcttggtgt atgacgttac tgacgagagg     300
tcgtttaaca gtgtacacaa ttggtaccag acattgaacc agcacgccaa tgaggacgcc     360
cagctgtttt tggtaggtaa caaatgtgat gacgaggagt ccagacaggt cactaaagag     420
caaggtgaac agttggctag tgagttaggt gttccattcc tggaagcttc ggccaagagt     480
aacaagaacg tggacgcaat cttttttggag ctagccaaac gattcgaaga gaagatgaga     540
aatacacaac agggccctgg ttctgctggt attgatgtaa attcctccaa cgacaccaaa     600
tcgtcttgtt gttga                                                     615

<210> SEQ ID NO 14
<211> LENGTH: 25
<212> TYPE: PRT
<213> ORGANISM: Artificial Sequence
<220> FEATURE:
<223> OTHER INFORMATION: WTSPGA N-terminus

<400> SEQUENCE: 14

Met Gln Leu Phe Asn Leu Pro Leu Lys Val Ser Phe Phe Leu Val Leu
1               5                   10                  15

Ser Tyr Phe Ser Leu Leu Val Ser Ala
            20                  25

<210> SEQ ID NO 15
<211> LENGTH: 15
<212> TYPE: PRT
<213> ORGANISM: Artificial Sequence
<220> FEATURE:
<223> OTHER INFORMATION: MSPGA N-terminus 1

<400> SEQUENCE: 15

Met Lys Phe Phe Leu Leu Leu Leu Leu Ile Gly Phe Cys Trp Ala
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: MSPGA N-Terminus 2

<400> SEQUENCE: 16

Val Ser Leu Glu Lys Arg Glu Ala Glu Ala
1               5                   10
```